United States Patent
Nguyen et al.

(10) Patent No.: US 8,478,388 B2
(45) Date of Patent: Jul. 2, 2013

(54) CARDIAC COORDINATE SYSTEM FOR MOTION ANALYSIS

(75) Inventors: Thao Thu Nguyen, Bloomington, MN (US); Kjell Norén, Solna (SE); Allen Keel, San Francisco, CA (US); Kyungmoo Ryu, Palmdale, CA (US); Stuart Rosenberg, Castaic, CA (US); Wenbo Hou, Lancaster, CA (US); Steve Koh, South Pasadena, CA (US); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 477 days.

(21) Appl. No.: 12/755,359

(22) Filed: Apr. 6, 2010

(65) Prior Publication Data

US 2011/0092809 A1    Apr. 21, 2011

Related U.S. Application Data

(60) Provisional application No. 61/167,453, filed on Apr. 7, 2009.

(51) Int. Cl.
*A61N 1/00* (2006.01)
*A61B 5/04* (2006.01)

(52) U.S. Cl.
USPC .............. 600/509; 600/508; 607/16; 607/17

(58) Field of Classification Search
USPC ................ 600/508–509, 512; 607/16–17
See application file for complete search history.

(56) References Cited

U.S. PATENT DOCUMENTS

| | | |
|---|---|---|
| 6,978,184 B1 | 12/2005 | Marcus et al. |
| 7,041,061 B2 | 5/2006 | Kramer et al. |
| 7,613,500 B2 | 11/2009 | Vass et al. |
| 2006/0235289 A1 | 10/2006 | Wesselink et al. |
| 2007/0135721 A1 | 6/2007 | Zdeblick |
| 2008/0058656 A1 | 3/2008 | Costello et al. |
| 2009/0018632 A1 | 1/2009 | Zdeblick et al. |
| 2009/0093857 A1 | 4/2009 | Markowitz et al. |
| 2009/0306732 A1 | 12/2009 | Rosenberg et al. |
| 2009/0318995 A1 | 12/2009 | Keel et al. |

FOREIGN PATENT DOCUMENTS

WO    2007111542 A1    10/2007

OTHER PUBLICATIONS

Abraham, William T. MD et al., "Cardiac Resynchronization in Chronic Heart Failure," N Engl J Med. Jun. 13, 2002; 346(24):1845-1853.

Ansalone, Gerardo MD et al., "Doppler Myocardial Imaging to Evaluate the Effectiveness of Pacing Sites in Patients Receiving Biventricular Pacing," J Am Coll Cardiol. 2002;39:489-499.

Becker, Michael et al., "Impact of left ventricular lead position on the efficacy of cardiac resynchronization therapy: a two-dimensional strain echocardiography study," Heart 2007;93:1197-1203.

(Continued)

*Primary Examiner* — Nicole F Lavert

(57) ABSTRACT

An exemplary method includes accessing cardiac information acquired via a catheter located at various positions in a venous network of a heart of a patient wherein the cardiac information comprises position information with respect to time for one or more electrodes of the catheter; performing a principal component analysis on at least some of the position information; and selecting at least one component of the principal component analysis to represent an axis of a cardiac coordinate system. Various other methods, devices, systems, etc., are also disclosed.

14 Claims, 20 Drawing Sheets

OTHER PUBLICATIONS

Bleeker, Gabe B. MD, PhD et al., "Left Ventricular Resynchronization Is Mandatory for Response to Cardiac Resynchronization Therapy: Analysis in Patients With Echocardiographic Evidence of Left Ventricular Dyssynchrony at Baseline," Circulation. 2007;116-1440-1448.

Chung, Eugene S. MD et al., "Results of the Predictors of Response to CRT (PROSPECT) Trial," Circulation. 2008;117:2608-2616.

Leitman, Marina MD et al., "Two-dimensional Strain—A Novel Software for Real-time quantitative Echocardiographic Assessment of Myocardial Function," J Am Soc Echocardiogr. 2004;17:1021-1029.

Macias, Alfonso et al., "Left ventricular pacing site in cardiac resynchronization therapy: Clinical follow-up and predictors of failed lateral implant," European Journal of Heart Failure. 2008;10:421-427.

Murphy, Ross T. MD et al., "Tissue Synchronization Imaging and Optimal Left Ventricular Pacing Site in Cardiac Resynchronization Therapy," Am J Cardiol. 2006;97:1615-1621.

Pan, C. et al., "Tissue Tracking Allows Rapid and Accurate Visual Evaluation of Left Ventricular Function," Eur J Echocardiography. 2001;2:197-202.

Singh, Jagmeet P. MD et al., "Left ventricular lead electrical delay predicts response to cardiac resynchronization therapy." Heart Rhythm. 2006;3:1285-1292.

Wilton, Stephen B. et al., "Relationship between left ventricular lead position using a simple radiographic classification scheme and long-term outcome with resynchronization therapy," J Interv Card Electrophysiol. 2008;23:219-227.

CARDIAC COORDINATE SYSTEM FOR MOTION ANALYSIS

RELATED APPLICATIONS

This application claims the benefit of U.S. Provisional Application having Ser. No. 61/167,453, filed Apr. 7, 2009, which is incorporated by reference herein.

TECHNICAL FIELD

Subject matter presented herein relates generally to electrode and lead-based investigation or therapy systems (e.g., cardiac pacing therapies, ablation therapies, sensing therapies, nerve stimulation therapies, etc.).

BACKGROUND

Despite advances in device technology, approximately one-third of patients fail to respond adequately to cardiac resynchronization therapy (CRT) (see, e.g., Abraham W T, Fisher W G, Smith A L, et al.: Cardiac resynchronization in chronic heart failure. N Engl J Med 2002; 346:1845-1853). Left ventricular lead placement is an important determinant of response, and conventional lead placement strategy is directed towards targeting the lateral or posterolateral branches of the coronary venous system (see, e.g., Macias A, Gavira J J, Castaño S, et al.: Left ventricular pacing site in cardiac resynchronization therapy: Clinical follow-up and predictors of failed lateral implant. Eur J Heart Fail 2008; 10:421-427; Wilton S B, Shibata M A, Sondergaard R, et al.: Relationship between left ventricular lead position using a simple radiographic classification scheme and long-term outcome with resynchronization therapy. J Interv Card Electrophysiol 2008; 23:219-227). Despite being a useful approach for positioning leads, a lack of response still exists in many patients.

Some data suggest that specifically targeting the region of maximal electrical delay could improve response to CRT (see, e.g., Singh J P, Fan D, Heist E K, et al.: Left ventricular lead electrical delay predicts response to cardiac resynchronization therapy. Heart Rhythm 2006; 3:1285-1292) while other data suggest that specifically targeting the region of maximal mechanical delay could improve response to CRT (see, e.g., Macias et al.; Becker M, Franke A, Breithard O A, et al.: Impact of left ventricular lead position on the efficacy of cardiac resynchronization therapy: a two-dimensional strain echocardiography study. Heart 2007; 93:1197-1203; Ansalone G, Giannantoni P, Ricci R, et al.: Doppler myocardial imaging to evaluate the effectiveness of pacing sites in patients receiving biventricular pacing. J Am Coll Cardiol 2002; 39:489-499; Murphy R T, Sigurdsson G, Mulamalla S, et al.: Tissue synchronization imaging and optimal left ventricular pacing site in cardiac resynchronization therapy. Am J Cardiol 2006; 97:1615-1621).

As described herein, various exemplary techniques acquire at least physiologic mechanical information and assess the information, for example, to enhance guidance of LV pacing site optimization during CRT implant. Various exemplary techniques may be applied to one or more types of therapy (e.g., cardiac pacing therapies, ablation therapies, sensing therapies, nerve stimulation therapies, etc.).

SUMMARY

An exemplary method includes accessing cardiac information acquired via a catheter located at various positions in a venous network of a heart of a patient wherein the cardiac information comprises position information with respect to time for one or more electrodes of the catheter; performing a principal component analysis on at least some of the position information; and selecting at least one component of the principal component analysis to represent an axis of a cardiac coordinate system. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
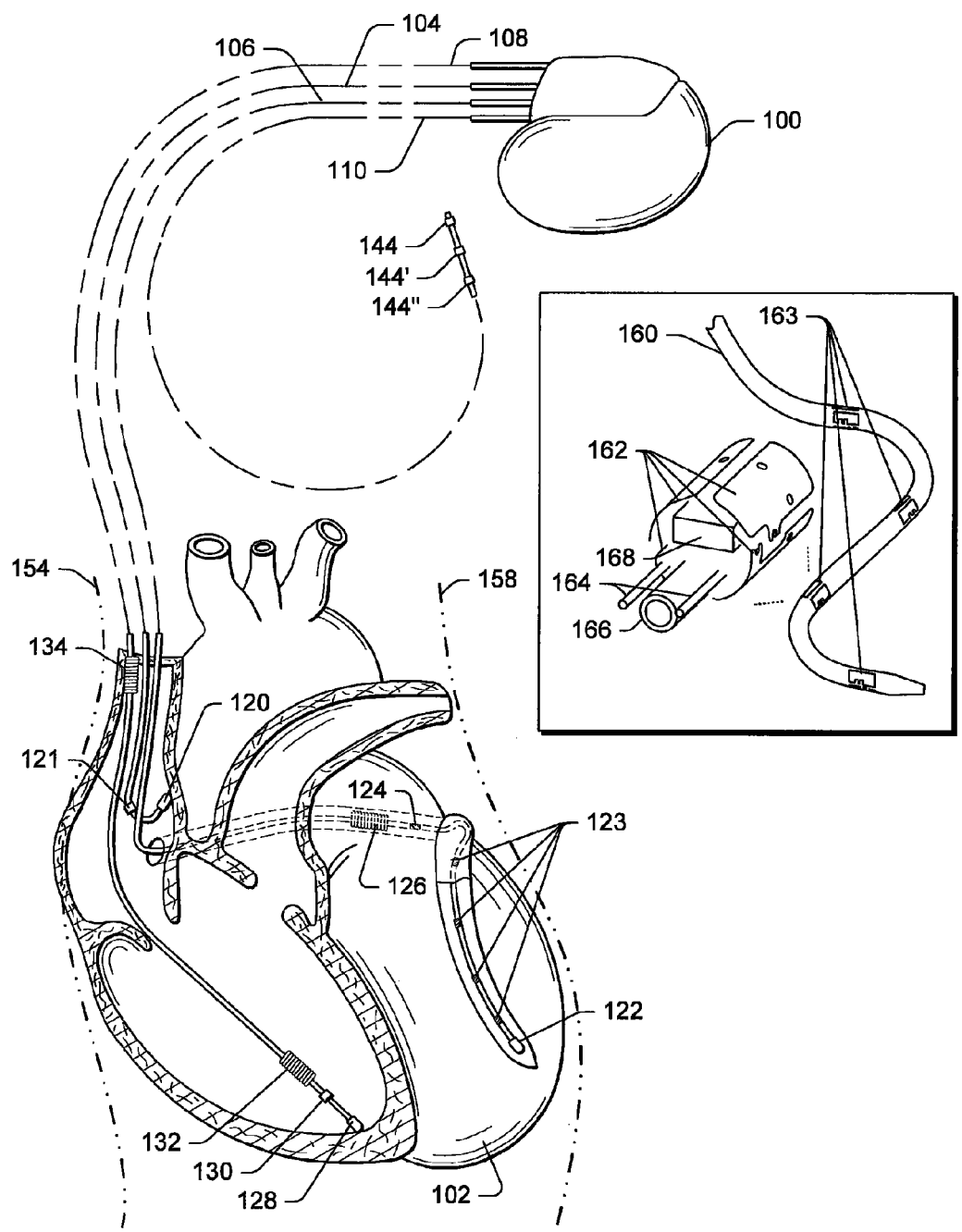
FIG. 1 is a simplified diagram illustrating an exemplary implantable stimulation device in electrical communication with at least three leads implanted into a patient's heart and at least one other lead for sensing and/or delivering stimulation and/or shock therapy. Approximate locations of the right and left phrenic nerves are also shown. Other devices with more or fewer leads may also be suitable for implementation of various exemplary techniques described herein.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are typically used to reference like parts or elements throughout.

Overview

Various exemplary techniques described herein pertain to analysis of electrode positions in the body. For example, during an intraoperative procedure, a clinician may maneuver an electrode-bearing catheter to various locations in one or more chambers or vessels of the heart and acquire position information. As described herein, various exemplary methods include determining a cardiac coordinate system based at least in part on acquired position information. For example, a principal component analysis of position information with respect to time can provide vectors (directions) that explain variance in position. Such vectors (directions) may also provide a basis for a cardiac coordinate system. In various examples, position information is transformed per a cardiac coordinate system to provide motion waveforms along a particular direction, or directions, to provide parameters, metrics, etc. As described herein, an exemplary method can determine one or more parameters with respect to a cardiac coordinate system where such parameters are analogs to conventional parameters (e.g., echocardiography parameters). Various cardiac coordinate system analyses may assist with treatment planning for a cardiac pacing therapy or other cardiac-related therapy.

As described herein, an exemplary system can be configured to assess motion of one or more leads in a patient's body by collected information from an implanted device (e.g., via telemetry) using, for example, a specialized localization system or an external computing device (e.g., a device programmer). Such a collection process may optionally occur at a standard CRT follow-up visit. An exemplary method can include comparing information collected post-implant to, for example, baseline information acquired pre-implant or at the time of implant. As described herein, such pre-implant information or time of implant information may be archived in memory of an implantable device or elsewhere (e.g., a database accessible by a device programmer, a localization system, etc.). Such a method may further include determining optimal settings for the implanted device (e.g., delays, electrode configuration, rates, etc.).

Various exemplary methods may be implemented, for example, using a pacing system analyzer (PSA) and a localization system or a specialized localization system. Various examples are described with respect to the ENSITE® NAVX® localization system (St Jude Medical, Atrial Fibrillation Division, Minnesota); noting that other types of localization systems may be used.

Various techniques aim to facilitate lead implantation, particularly for leads that enter the coronary sinus to reach distal branches thereof. For example, various techniques can allow a clinician to view plots or maps of one or more metrics in association with a patient's anatomy and readily decide to locate a lead in an anatomical region with acceptable or optimal metrics for delivery of a cardiac therapy. A typical intraoperative, acute state process occurs iteratively (i.e., select or move, acquire, calculate; select or move, acquire, calculate; . . . ). In this iterative process, a clinician may note whether an anatomical location (e.g., in a venous network) is associated with one or more acceptable metrics or unacceptable metrics.

As described herein, various exemplary techniques can be used to make decisions as to cardiac pacing therapy and optimization of a cardiac pacing therapy (e.g., CRT or other pacing therapies). In a clinical trial, acute resynchronization was shown to be a significant factor in assessing CRT efficacy and long-term outcome[1]. Various methods described herein, build on this clinical finding by formulating specialized techniques and metrics associated with locations for pacing, sensing or pacing and sensing. In turn, a clinician can assess how a particular CRT therapy or configuration thereof may be expected to perform at time of implant or, in some instances, after implant.

[1] G B Bleeker, S A Mollema, E R Holman, N Van De Veire, C Ypenburg, E Boersma, E E van der Wall, M J Schalij, J J Bax. "Left Ventricular Resynchronization is Mandatory for Response to Cardiac Resynchronization Therapy: Analysis in Patients with Echocardiographic Evidence of Left Ventricular Dyssynchrony at Baseline". *Circulation* 2007; 116: 1440-1448.

An exemplary stimulation device is described followed by various techniques for acquiring information and defining a cardiac coordinate system. The drawings and detailed description elucidate details of various techniques that may be used singly or in combination during an assessment or an optimization process (e.g., acute or chronic).

Exemplary Stimulation Device

Figure 2:
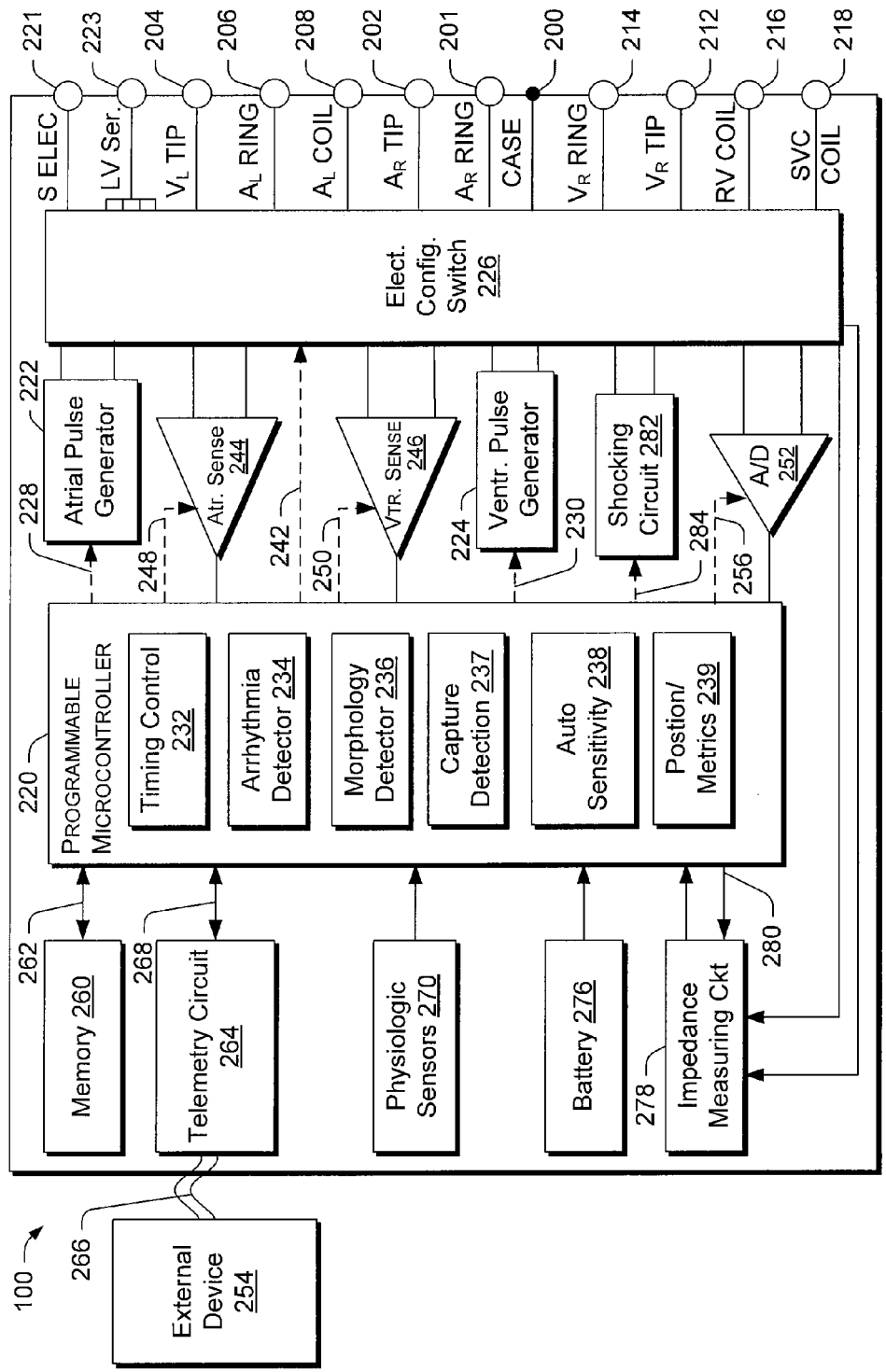
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

Various techniques described below may be implemented in connection with a device configured or configurable for cardiac therapy, nerve therapy or one or more other types of therapy. With reference to FIGS. 1 and 2, an exemplary stimulation device is described, for example, configured or configurable for delivery of one or more types of cardiac stimulation therapy.

FIG. 1 shows an exemplary stimulation device 100 in electrical communication with a patient's heart 102 by way of three leads (a right atrial lead 104, a left ventricular lead 106 and a right ventricular lead 108), suitable for delivering multi-chamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144" suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibres for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the left side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart.

Housing 200 for the device 100 is often referred to as the "can", "case" or "case electrode", and may be programmably selected to act as the return electrode for all "unipolar" modes. As described below, various exemplary techniques implement unipolar sensing for data that may include indicia of functional conduction block in myocardial tissue. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

The microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional position and/or metrics module 239. The module 239 may be used for purposes of acquiring position information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor electrode positions and cardiac mechanics in relationship to cardiac electrical activity and may help to optimize cardiac resynchronization therapy. The module 239 may include instructions for vector analyses, for example, based on locally acquired or transmitted position information. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart.

Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, oxygen concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
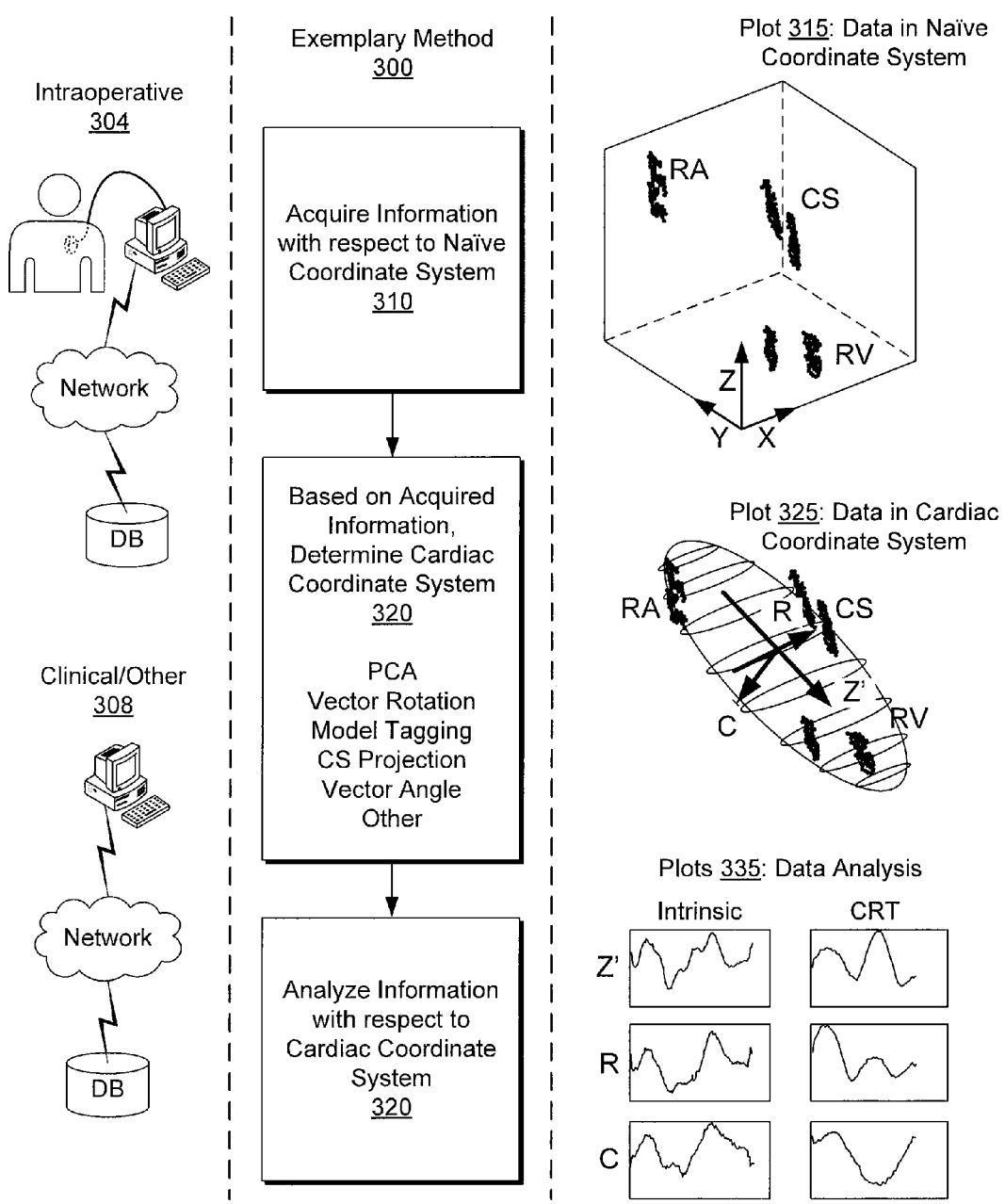
FIG. 3 is a block diagram of an exemplary method for determining a cardiac coordinate system and analyzing information with respect to the cardiac coordinate system.

FIG. 3 shows an exemplary method 300 for transforming acquired information and for analyzing the transformed information. The method 300 is shown with respect to an intraoperative setting 304 and a clinical or other setting 308. The intraoperative setting 304 includes a system for acquiring information, for example, by placing a catheter in a patient's body. The system may be configured to transmit acquired information to a data storage (e.g., database), for example, via a network. The clinical (or other) setting 308 includes a computing device configured to at least analyze information and optionally transform information. The system of the clinical setting 308 may perform such actions on information acquired by a system in the intraoperative setting 304, for example, where such information is stored in a database, a removable storage medium, or communicated to the system of the clinical setting 308.

In the example of FIG. 3, the method 300 includes an acquisition block 310 that acquires information with respect to a naïve coordinate system (e.g., a Cartesian coordinate system X, Y, Z). For example, a plot 315 shows data in a naïve coordinate system where the data includes right atrial (RA) electrode motion data, coronary sinus (CS) electrode motion data and right ventricular (RV) electrode motion data. In a determination block 320, the method 300 determines a cardiac coordinate system (i.e., non-naïve coordinate system) based at least in part on the acquired information. Examples of some techniques include principal component analysis (PCA), vector rotation (see, e.g., FIG. 6), model tagging (see, e.g., FIG. 7), coronary sinus projection (see, e.g., FIG. 8) and vector angle (see, e.g., FIG. 9). A plot 325 shows the acquired data in a cardiac coordinate system (CCS) (e.g., a cylindrical coordinate system Z', R, C). In this example, the axis Z' is aligned with the direction of largest variance of the acquired data. In an analysis block 330, the method 300 analyzes the information with respect to the CCS. Plots 335 show position versus time data along the Z' axis, the R axis and the circumferential (azimuthal) angle C with respect to time for intrinsic activation of the heart and for biventricular paced activation of the heart (CRT). As described herein, analysis of data in a patient specific CCS can provide insight into cardiac mechanics and assist placement of one or more electrodes for delivery of a cardiac therapy (e.g., stimulation, sensing, etc.). Further, such an analysis may help to set or adjust one or more therapy parameters (e.g., stimulation parameters such as timing, energy, duration, polarity, delays, etc.). Yet further, such an analysis may help diagnose one or more cardiac conditions (e.g., based on trends, comparisons to other patient data, types of motion, lack of motion, etc.).

As described herein, various exemplary methods may rely on principal component analysis (PCA) to define a cardiac coordinate system (CCS) based on data acquired with respect to a naïve coordinate system (NCS).

PCA may be viewed as a variable reduction procedure, particularly useful for analyzing data obtained for a number of variables (possibly a large number of variables) where some redundancy is believed to exist amongst those variables. In this case, redundancy means that some of the variables are correlated with one another, possibly because they are measuring the same construct. Due to redundancy, it should be possible to reduce the observed variables into a smaller number of principal components (sometimes referred to as "artificial" variables) that can account for most of the variance in the observed variables. As described herein, PCA is used to determine a cardiac coordinate system that accounts for variance in cardiac motion, for example, to find a principal component that describes most of the directional motion of the heart. For example, an exemplary PCA analysis may provide insight as to cardiac motion related to body position, drug administration, intrinsic activation, atrial pacing, right ventricular pacing, left ventricular pacing, biventricular pacing, other multi-chamber pacing, etc.

In PCA, the first component extracted accounts for a maximal amount of total variance in the observed variables; in general, the first component will be correlated with at least some of the observed variables and it may be correlated with many. The second component extracted accounts for a maximal amount of variance in the data set that was not accounted for by the first component, which, in general, means that the second component will be correlated with some of the observed variables that did not display strong correlations with first component. Also, in general terms, the second component will be uncorrelated with the first component (i.e., the correlation between the first and second components should be zero). Other remaining components extracted via PCA display the same two characteristics as the second component: each component accounts for a maximal amount of variance in the observed variables that was not accounted for by the preceding components, and is uncorrelated with all of the preceding components. As each additional component accounts for progressively smaller and smaller amounts of variance, in general, the first few components are usually relied on for interpreting the data.

In general, PCA makes no assumption about an underlying causal model. However, as described herein, cardiac mechanics may be considered as being more readily represented in a cylindrical or coordinate system other than a Cartesian coordinate system. In various examples, a naïve coordinate system (NCS) is Cartesian and a cardiac coordinate system (CCS) is cylindrical. As described herein, one or more other types of coordinate systems suitable for modeling cardiac mechanics may be used as a CCS (e.g., spherical, oblate spherical, prolate spherical, etc.). For example, the heart may be modeled as a spheroid or a chamber of the heart may be modeled as a spheroid. As the left ventricle provides significant pumping action, an analysis may focus on the left ventricle modeled, for example, as a cylinder or a prolate spheroid. In such an example, a prolate spheroid model may be fit to acquired information and optionally a coordinate system extracted from the fit prolate spheroid model (e.g., to provide a non-naïve coordinate system). A fitting process may include providing one or more non-linear equations with associated parameters to define a prolate spheroid or a portion thereof and, for example, applying a least-squares technique to minimize error between data and a value of an equation (or values of equations).

With respect to an image-based localization technique with a naïve 3-D coordinate system (X, Y, Z), consider measurements of electrode motion being recorded in three naïve planes XY, XZ and YZ associated with, for example, a fluoroscopic technique (e.g., projections from three observation points). For an exemplary PCA scheme, each electrode may be viewed as moving in the dimensions defined by each of the three planes (i.e., six measurement dimensions, two for each plane). In such a scheme, every position-time sample for an electrode may be viewed as a vector (e.g., with respect to a root or null position) in a space spanned by some orthonormal basis. As described herein, the underlying orthonormal basis can be determined using an exemplary PCA scheme. Specifically, such a PCA scheme can re-express each of the original samples through a linear combination of orthonormal basis vectors (e.g., to define a CCS).

As an example, let A be an original data set, where each column is a single sample (or moment in time) of the data set. In an electrode example, A is an m×n matrix where m=M (number of dimensions) and n=N (total number of samples). Let B be another m×n matrix related by a linear transformation P. A is the original recorded data set and B is a re-representation of that data set: PA=B where P is a matrix that transforms A into B (e.g., geometrically, P is a typically a rotation and a stretch that transforms A into B). The rows of P, $\{p_1, \ldots, p_m\}$, are a set of new basis vectors for expressing the columns of A. In other words, the rows of P are a new set of basis vectors for representing columns of A.

With respect to a cardiac coordinate system (CCS), directions with largest variances in a measurement vector space are assumed to contain dynamics of interest. Further, the direction with the largest variance may be presumed to have the highest signal-to-noise ratio (SNR). In contrast, a coordinate system of the naïve basis (e.g., X, Y, Z coordinate system) is unlikely to have any of its axes correspond to the direction of largest variance. As to this point, an exemplary PCA approach that defines one or more axes of a cardiac coordinate system can optionally be used to alleviate some uncertainty for placement of patches of a localization system. For example, once an orthonormal basis is found for a particular patient (or more generally for a population of patients), a clinician may place patches, fluoroscopic equipment, etc., in a manner to more closely align a naïve basis of a localization system (e.g., image-based, electrical signal-based, etc.) to an underlying physiologic orthonormal basis that accounts for cardiac motion.

Referring to the matrices A and B, an exemplary PCA scheme can include selecting a normalized direction in m-dimensional space along which variance in A is maximized and saving this vector as $p_1$. Next, the scheme can include finding another direction along which variance is maximized, however, because of the orthonormality condition, a search can be restricted to all directions perpendicular to all previous selected directions. The resulting vector may then be saved as $P_i$. The process as to $p_i$ can be repeating until m vectors are selected. Accordingly, the resulting ordered set of p's are the principal components. Such a process is amenable to solution by linear algebra as there exist decompositions that can provide efficient, explicit algebraic solutions (e.g., based on eigenvector decomposition or singular value decomposition).

A particular approach may be summarized as finding some orthonormal matrix P where B=PA such that the covariance matrix $Cov_B \equiv (n-1)^{-1} BB^T$ is diagonalized and the rows of P are the principal components of A. Other types of component analysis include independent component analysis (ICA). Further, techniques that account for known behavior (e.g., known mechanics or theoretical mechanics) may be relied on, for example, to transform sample data prior to a component analysis. For example, sample data may be transformed from a naïve Cartesian coordinate system to what may be considered a less "naïve" cylindrical coordinate system where rotational motion is known to exist. Analyses involving principal curves or manifolds may help to explain natural geometry (e.g., to extend geometric interpretation of PCA).

As described herein, an intraoperative exploration procedure to acquire information relies on acquisition equipment. For example, an exploration procedure may rely on a localization system such as the ENSITE® NAVX® system or other system with appropriate localization features. The ENSITE® NAVX® localization system includes patch electrodes for placement on a patient's body that can establish a multidimensional localization field (e.g., by delivery of current using patch electrodes). Given a localization field, the ENSITE® NAVX® system can use an electrode positioned in the body of the patient to measure electrical potential and, in turn, to determine a position for the electrode. Where an electrode is positioned in a cardiac space (e.g., cardiac surface, cardiac chamber, cardiac vein, etc.), the ENSITE® NAVX® system can acquire electrical potential with respect to time to generate a mechanical waveform indicative of cardiac motion. Such a waveform may be analyzed (or acquired) with respect to electrical information, for example, to determine position, displacement, velocity, acceleration, etc., of an electrode in response to cardiac motion (e.g., peak systolic, peak diastolic, etc.).

Acquired information can include electrical information such as electrical activation times and cardiac potentials and mechanical information such as mechanical activation times, motion waveforms, path length, velocity, etc. Such information may be acquired or determined with respect to anatomic features such as a venous network of the heart. The primary venous network of the heart includes the coronary sinus, which empties into the right atrium via the coronary sinus ostium. The coronary sinus network drains about 95% of the venous blood of the myocardium (the remaining 5% of myocardial venous flow drains through the thebesian vessels).

The coronary sinus has various tributary veins including the small, middle, great and oblique cardiac veins, the left marginal vein and the left posterior ventricular vein. The great cardiac vein is normally the longest venous vessel of the heart. The great and the middle cardiac veins normally merge at the apex of the heart, forming together with the coronary sinus, a fairly complete venous ring around the left ventricle. Consequently, these tributaries of the coronary sinus are often considered as candidates when deciding where to place a lead for electrical activation of the left ventricle.

In general, the extent of exploration of a venous network depends on catheter characteristics. For example, a catheter with a large cross-sectional dimension or high rigidity may be suited for navigation of the coronary sinus but only partial navigation of one or more tributaries of the coronary sinus. In contrast, leads typically configured for stimulation therapies have small cross-section dimension and are quite flexible to allow for deep access to the heart's venous network.

In some instances, a catheter may be configured to acquire data such as temperature or flow (e.g., thermodilution). In such instances, flow, temperature or other data may be acquired. While blood from the coronary sinus drains to the heart, flow to the coronary sinus still effectively transports heat energy to aid in cooling the heart. Various studies demonstrate relationships between flow in the coronary sinus or tributaries thereof with conditions such as ischemia. Such information may help localize ischemia and, as described herein, improve selection of an appropriate venous branch for locating one or more lead-based electrodes, sensors or other therapeutic equipment. Where such information is localized using a localization system, the information may be mapped or otherwise presented or analyzed in conjunction with localized electrical information, mechanical information, etc. Accordingly, a rich understanding of a patient's venous network, particularly the coronary sinus, may be attained.

Referring again to FIG. 3, an analysis of information with respect to a cardiac coordinate system may be used, optionally in combination with other information, to determine one or more locations for placement of a lead, placement of a sensor, placement of ablation therapy equipment, placement of nerve therapy equipment, etc.

As mentioned, a localization system such as the ENSITE® NAVX® system may be used to acquire position information. Further, a localization system may include analysis features that allow for essentially real-time display of information as such information is acquired and optionally analyzed during an exploration of the venous network of a patient. As described herein, real-time information may be mapped in conjunction with previously acquired information (e.g., prior intraoperative exploration or image information from CT, MR or ultrasound studies).

During an information acquisition procedure, a clinician may explore a venous network while delivering electrical energy to stimulate the heart, for example, as indicated in the plots 335 of FIG. 3 for intrinsic and CRT. Further, delivery parameters may be varied to determine whether a location in a selected tributary of the coronary sinus is suitable for a therapy. For example, with respect to a stimulation therapy, a clinician may vary polarity, energy level, pulse shape, pulse duration, etc., during a procedure while acquiring position information (e.g., electrical potentials measured in a localization field). Where a procedure includes inserting multiple electrode-bearing leads, various electrodes on those leads may be used to acquire position information, for example, to understand cardiac mechanics responsive to the delivered stimulation energy. Further, such electrodes may acquire potentials associated with cardiac activity. Accordingly, an analysis process may generate dynamic diagnostics of mechanical and electrical information and render diagnostic information to a display in near real-time to allow a clinician to expeditiously explore a tributary to the coronary sinus and select an optimal location for therapeutic equipment (e.g., an electrode, a sensor, an ablation device, etc.).

In a post-implant or chronic phase, a follow-up procedure may take place in a clinical setting to acquire data and verify or optimize parameters associated with a therapy that relies on an implantable device. Depending on the capabilities of the device and clinical equipment, various types of information may be acquired. As explained with respect to the device 100 of FIGS. 1 and 2, a typical cardiac stimulation device is configured for telemetric communication with an external device, sometimes referred to as a device programmer. The device may transmit acquired information to an external device and respond to instructions received from an external device. An implanted device may transmit IEGMs (electrical information) as well as other information (e.g., depending of device capabilities). For example, with respect to mechanical information, the implanted device may include an accelerometer, impedance circuitry, etc., which may be used to acquire information related to cardiac mechanics. An implanted device or an external device may assess cardiac performance based on acquired information. In turn, one or more therapy parameters may be verified or optimized. Further, depending on the clinical setting, echocardiography, CT or other equipment may be available to acquire information to aid in an assessment of cardiac performance, implanted device performance, etc. Yet further, an external system may be available to generate a localization field where implanted electrodes can measure electrical potential in the localization field. Where such a system is available, a follow-up procedure may include verification or optimization based on such position information (e.g., akin to the aforementioned ENSITE® NAVX® system analyses).

As described herein, where an exemplary coronary sinus analysis technique is used to enhance a cardiac stimulation therapy, one may expect values for time from RV pace to electrical activation of the LV to become more homogeneous after commencement of CRT therapy. Further, an analysis of information acquired from an exploration of a venous network may provide an indication of potential CRT efficacy or response and optionally, after delivery of CRT, such an analysis may help to determine whether a patient is a CRT responder. In addition, where electrode position can be determined post-implant, lead motion data may be compared to baseline measurements taken at the time of coronary sinus mapping or CRT implant (or both).

After implantation and between follow-up visits, a device-based acquisition process may acquire various types of information including electrical information and optionally mechanical information. An implanted device may be configured to acquire information and to verify or optimize one or more parameters based on such information. For example, the QUICKOPT® algorithm (St. Jude Medical, Inc.) can allow for device-based verification or optimization of AV and VV delays based on acquired electrical information.

As described herein, data acquired during an intraoperative procedure and data acquired post-implant (e.g., chronic data), or analyses based on such data, may be stored in a database. Where a database stores data or analyses for many patients, it may be relied on during any of the various stages of therapy planning and delivery. Information may be used to track progress of a patient over time. Further, a trend for a patient or implanted device may be compared to trends for other patients or other implanted devices. As to storage, information may be stored in an implantable device, a programmer configured with storage, a networked storage device, a removable storage device (e.g., a memory card), etc. Where an implantable device stores data, the data may be relied on in making decisions as to delivery of therapy (e.g., setting one or more therapy parameters, trend analysis, etc.).

Figure 4:
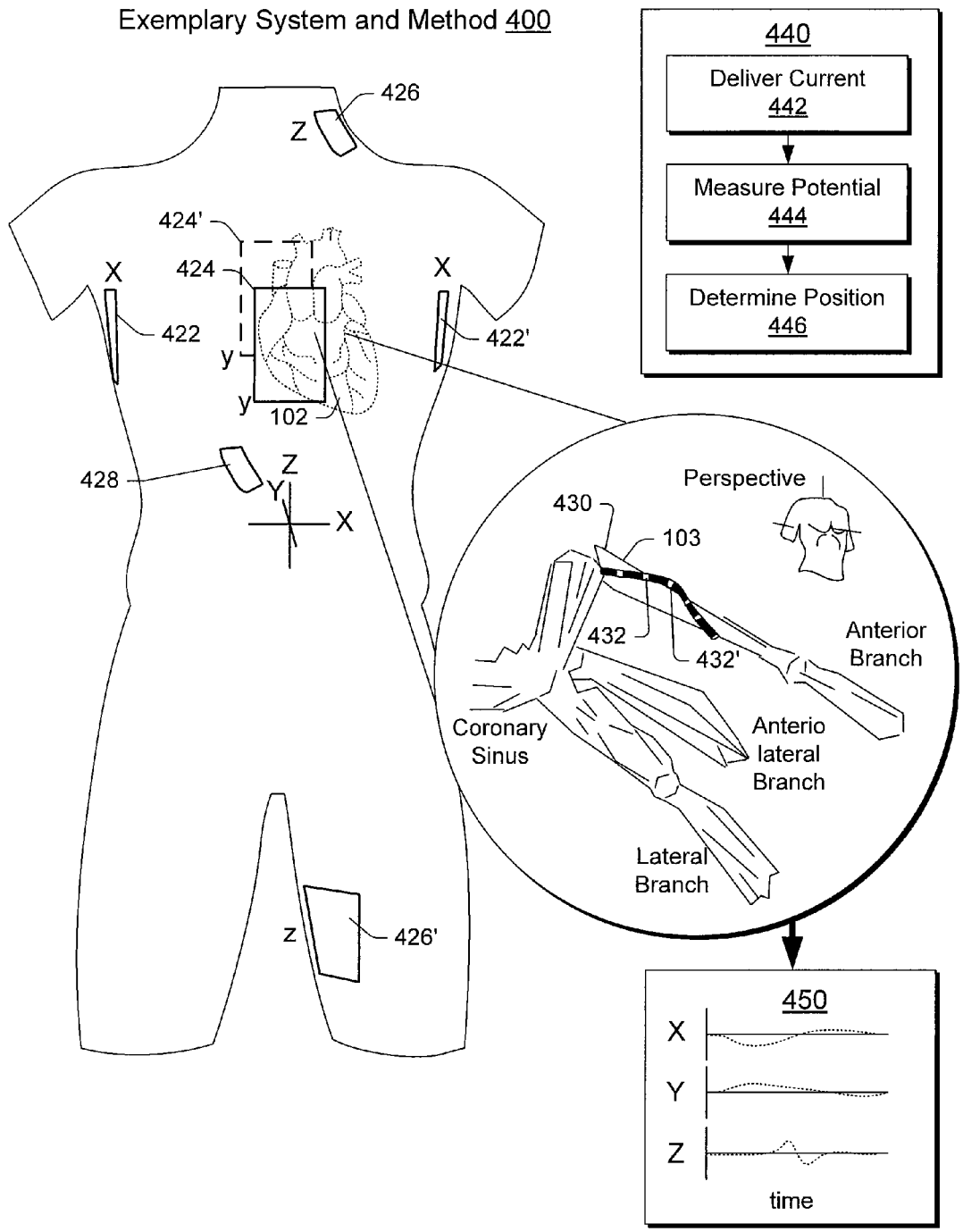
FIG. 4 is a diagram of an exemplary arrangement of leads and electrodes for acquiring data and exemplary data and metrics based on the acquired data.

FIG. 4 shows an arrangement and method 400 that may rely in part on a commercially available system marketed as ENSITE® NAVX® navigation and visualization system (see also LOCALISA® system, Medtronic, Inc., Minnesota). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 4, electrodes 432, 432', which may be part of a standard EP catheter 430 (or lead), sense electrical potential associated with current signals transmitted between three pairs of surface electrode patches 422, 422' (X-axis), 424, 424' (Y-axis) and 426, 426' (Z-axis). An addition electrode patch 428 (sometimes referred to as a "belly" patch) is available for reference, grounding or other function. The ENSITE® NAVX® system can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body (e.g., to define a naïve coordinate system). The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 440, a system (e.g., such as the ENSITE® NAVX® system) delivers low level separable currents from the three substantially orthogonal electrode pairs (422, 422', 424, 424', 426, 426') positioned on the body surface (delivery block 442). The specific position of a catheter (or lead) electrode within a chamber of the heart can then be established based on three resulting potentials measured between the recording electrode with respect to a reference electrode, as seen over the distance from each patch set to the recording electrode (measurement block 444). Sequential positioning of a catheter (or lead) at multiple sites along the endocardial surface of a specific chamber can establish that chamber's geometry, i.e., position mapping (position determination block 446). Where the catheter (or lead) 430 moves (e.g., due to cardiac mechanics), the method 440 may also measure motion.

In addition to mapping at specific points, the ENSITE® NAVX® system provides for interpolation (e.g., for mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component.

With respect to motion (e.g., change in position with respect to time), the exemplary system and method 400 may track motion of an electrode in one or more dimensions. For example, a plot 450 of motion versus time for three dimensions (X, Y, Z) corresponds to motion of one or more electrodes of the catheter (or lead) 430 positioned in a vessel 103 of the heart 102 where the catheter (or lead) 430 includes the one or more electrodes 432, 432'. Motion of the catheter (or lead) 430 may exhibit hysteresis over a cardiac cycle. For example, a systolic path may differ from a diastolic path. An exemplary method may analyze hysteresis for any of a variety of purposes including assessing stability of an electrode of a catheter (or lead), assessing stability of a catheter (or lead), selection of a stimulation site, selection of a sensing site, diagnosis of cardiac condition, etc.

The exemplary method 440, as mentioned, includes the delivery block 442 for delivery of current, the measurement block 444 to measure potential in a field defined by the delivered current and the determination block 446 to determine position or motion based at least in part on the measured potential. According to such a method, position or motion during systole and/or diastole may be associated with electrical information or other information (e.g., biosensor, loading of a catheter or lead, intrinsic/paced activation, etc.). Alone, or in combination with other information, the position or motion information may be used for various assessments (e.g., stability assessments), selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 400 may use one or more features of the aforementioned ENSITE® NAVX® system. For example, one or more pairs of electrodes (422, 422', 424, 424', 426, 426' and optionally 428) may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 432, 432').

The exemplary system 400 may be used to track position or motion of one or more electrodes due to systolic function, diastolic function, respiratory function, etc. Electrodes may be positioned along the endocardium and/or epicardium during a scouting or mapping process for use in conjunction with electrical information. Such information may also be used alone, or in conjunction with other information (e.g., electrical information), for assessing stability of an electrode or electrodes for use in delivering a therapy or for identifying the optimal location of an electrode or electrodes for use in delivering a therapy. For example, a location may be selected for optimal stability, for optimal stimulation, for optimal sensing, or for other purposes.

With respect to stimulation, stimulation may be delivered to control cardiac mechanics (e.g., contraction of a chamber of the heart) or nerve action and position or motion information may be acquired where such information is associated with the controlled cardiac mechanics or controlled nerve action; noting that other types of interventions may also be applied (e.g., body position, drugs, etc.). An exemplary selection process may identify the best stimulation site based on factors such as electrical activity, electromechanical delay, extent of motion, synchrony of motion where motion may be classified as motion due to systolic function or motion due to diastolic function. In general, cardiac motion information corresponds to motion of an electrode or electrodes (e.g., endocardial electrodes, epicardial electrodes, etc.) and may be related to motion of the heart or other physiology. In instances pertaining to nerve stimulation therapy, motion may be, for example, respiratory motion (e.g., diaphragm motion due to stimulation of a phrenic nerve).

As described with respect to FIG. 4, a localization system can acquire position information for one or more electrodes on a lead or catheter. The ENSITE® NAVX® system can operate at a sampling frequency around 100 Hz (10 ms), which, for a cardiac rhythm of 60 bpm, allows for 100 samples per electrode per cardiac cycle. In various examples, sampling may be gated to occur over only a portion of a cardiac cycle. Gating may rely on fiducial markers such as peaks, gradients, crossings, etc., in an electrogram of heart activity. Other techniques for gating can include accelerometer techniques, impedance techniques, pressure techniques, flow techniques, etc. For example, an accelerometer signal slope above a threshold value (e.g., due to cardiac contraction or relaxation) can be used to commence acquisition of information or to terminate acquisition of information during a cardiac cycle. Such a technique may be repeated over multiple cardiac cycles with or without application of electrical stimuli, medication, body position changes, etc.

As described herein, for one or more electrodes, a localization system can provide four-dimensional information (e.g., X, Y, Z and time). The four-dimensional information describes a three-dimensional trajectory in space that can be analyzed or displayed in part, in whole or at one or more key points in time. As mentioned, various other types of information may be used to gate acquisition or to delineate points or segments of a trajectory. For example, information provided by a surface ECG, an intracardiac EGM (IEGM), or other biosignal can delineate a point or event such as QRS onset or pacing pulse or a segment (e.g., QRS complex, QT interval, etc.).

Where an electrode is position in a vessel of the heart such as a vein (e.g., CS or a tributary thereof), the trajectory of the electrode will follow cardiac motion of nearby myocardium. For example, a CS lead electrode will trace the path traversed by epicardium adjacent the CS or adjacent the particular CS tributary. If the lead position is stable in a branch, the trajectory for consecutive beats will typically remain within a bounded spatial volume; however, if the lead dislodges grossly, a shift in the CS lead electrode's position will be apparent in a display or analysis of the acquired information.

In various instances, depending on placement of electrodes that generate a localization field, respiration may affect accuracy of position data. For example, referring to FIG. 4, as a patient breathes, the torso changes shape, which can alter the alignment of the electrodes 422, 422', 424, 424', 426, 426' and 428. Further, as respiration introduces air into the body, dielectric properties of media between electrodes of a directional pair may change. To account for the affects of respiration, an exemplary data acquisition technique may include an algorithm that compensates for respiratory motion. Alternatively, compensation of filtering may be performed after data acquisition, for example, using one or more algorithms that identify frequencies in data that are likely related to respiration and adjust the data (e.g., filter or normalize) to compensate for respiration. In other instances, respiration gating may be used during data acquisition, for example, akin to techniques used during acquisition of nuclear magnetic resonance data (e.g., NMR or MRI data). For example, beats to be included in a stability index metric may be gated to a particular portion of the respiratory cycle.

As described herein, an exemplary method that relies on a component analysis (e.g., PCA) may find one or more components associated with respiration. For example, if a catheter is placed in at a location (e.g., in a vein) that moves with respect to respiratory movement and minimally with respect to cardiac motion, PCA may determine a direction (e.g., an axis) that accounts for variance associated with respiratory movement. As described herein, motion detected along a respiratory direction may optionally be used for gating (e.g., defining a window) or one or more other purposes.

The ENSITE® NAVX® system includes a so-called "RespComp" algorithm that uses a combination of impedance between various pairs of patches, which create the localization field, as a measure of respiratory motion. In yet another alternative, motion of electrodes that are known to be stable can be used to ascertain respiratory motion. For example, position data with respect to time may have low frequency content (approximately 0.1 Hz to approximately 0.5 Hz) that can be due to respiration, which can be subtracted from the motion of the electrode of which stability is of interest.

Instantaneous fluid status, among other variables, can cause some drift in position as measured by a localization system such as the ENSITE® NAVX® system. An exemplary method can include a correction factor that accounts for fluid status drift, which may be found by comparing position of a stable electrode from one cycle to the next and applying any measured offset to an electrode of interest.

As described herein, for various vector metrics, subtraction techniques or other techniques may act to reduce or eliminate fluid status contributions or movement contributions caused by respiration, the heart in the body (e.g., within a localization field) or by patient movement (e.g., change in posture, etc.).

As mentioned, a particular exemplary approach uses principle component analysis (PCA), which can rely on variations in all electrode motions to determine cardiac axes. For example, the axis in which the greatest amount of variation is found can be defined as the long axis (primary contraction mechanism), the axis in which the second greatest amount of variation is found can be defined as the short axis (secondary contraction mechanism), and the axis in which the third greatest amount of variation is found can be defined as the normal axis (tertiary contraction mechanism). As described herein, PCA may be used to uncover one or more directions associated with respiratory motion (e.g., optionally accounting for respiratory frequency). An exemplary method may include instructing a patient to inhale/exhale to assist with an analysis to determine one or more directions associated with respiratory motion (e.g., by time marking data, providing an inhalation window, providing an exhalation window, etc.)

An exemplary transformation method can find a "best" geometrical fit where the sum of the orthogonal distances to the original localization system LPS (X, Y, Z) data is minimized (see, e.g., naïve coordinate system of FIG. 4). If V0 is the centroid position, then:

0) V0 is the best fitted constant
1) $V0+k1*V1$ is the best fitted line
2) $V0+k1*V1+k2*V2$ is the best fitted plane
3) $V0+k1*V1+k2*V2+k3*V3$ is the best fitted space where k1, k2, k3 are scalars, V1 is the LV long-axis, and V2 is the LV short-axis.

Another approach of this analysis includes the PCA of individual electrodes to define electrode specific long, short, and normal axis mechanical motion of said electrodes.

Figure 5:
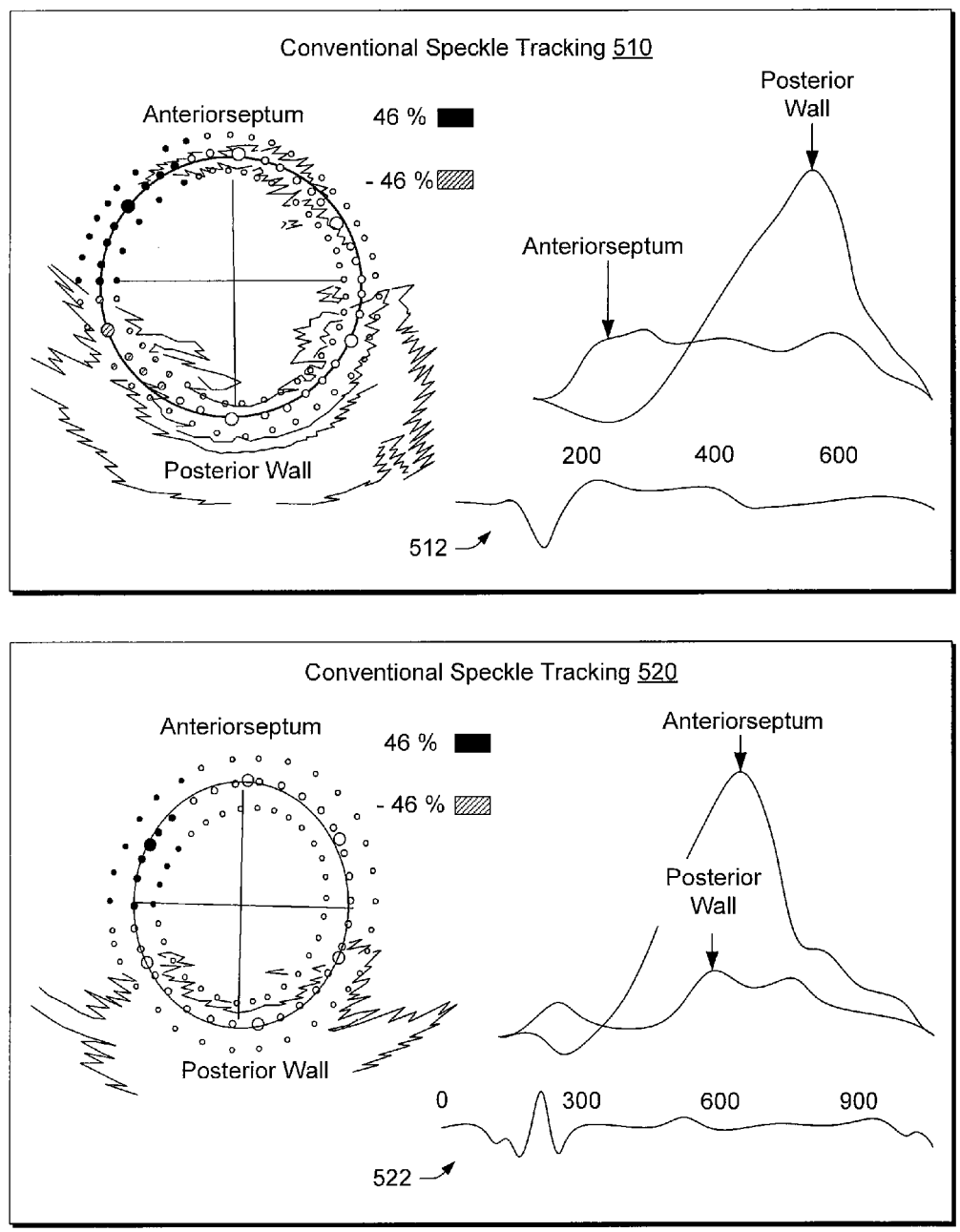
FIG. 5 is a diagram of information acquired and analyzed according to conventional echocardiography techniques.

FIG. 5 shows data presentations 510, 520 from conventional echocardiographic speckle tracking analyses that track motion of selected "speckles", which are then analyzed along the radial plane of the heart (e.g., transverse plane). The presentation 510 corresponds to paced activation of the heart (see ECG 512) while the presentation 510 corresponds to intrinsic activation of the heart (see ECG 522).

As described herein, an exemplary method can transform data acquired via a localization system that relies on one or more indwelling electrodes to another format that provides for analyses comparable to those of echocardiography. For example, by transforming position information from a naïve coordinate system (NCS) to a cardiac coordinate system (CCS), the localization system data may provide metrics comparable to echocardiographic tissue Doppler imaging (TDI) and speckle tracking. TDI measures regional wall motion velocities along a longitudinal axis while speckle tracking selects point locations of myocardium to track from frame to frame to evaluate strain, strain rate, tissue velocity, and LV rotation as shown in FIG. 5.

As explained, a naïve coordinate system (NCS) is often independent of the orientation or motion of the heart. To better assess electrode motion based upon separate components of motion (e.g., longitudinal, radial, circumferential, or x', y', and z') a cardiac coordinate system can minimize signal attenuation due to cardiac orientation.

Transforming localization system data into cylindrical coordinates provides a more accurate and intuitive method of analyzing motion data. In addition, data are more representative of current standards for measurement of mechanical motion such as standards associated with echocardiography.

Figure 6:
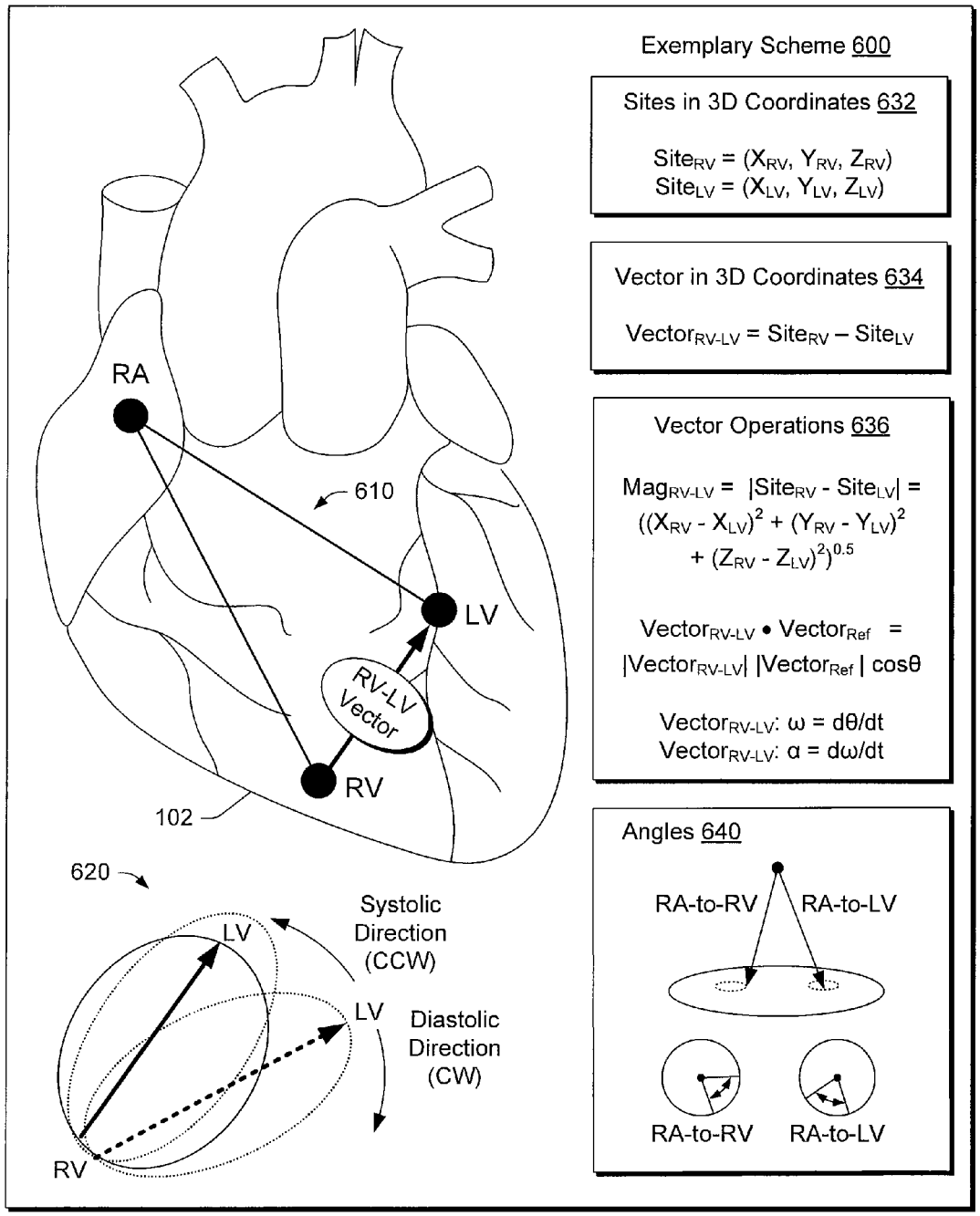
FIG. 6 is a diagram of the heart along with various vectors that may be used to define a cardiac coordinate system.

FIG. 6 shows a diagram of an exemplary transform scheme 600 that relies on a RV-to-LV vector. In FIG. 6, a triangle 610 is shown with respect to the heart 102. The vertices of the triangle include a right atrial point (RA), a right ventricular point (RV) and a left ventricular point (LV). A diagram 620 illustrates movement of the RV-to-LV vector during a cardiac cycle. Specifically, when the heart 102 contracts, the vector from the RV point to the LV point rotates in a counter-clockwise direction during systole and rotates in clockwise direction during diastole. Trial data indicate that, at the end of systole, length of the RV-to-LV vector reaches a minimum while angle of rotation from delivery of a pacing stimulus (V-pulse) reaches a maximum. In the example of FIG. 6, the diagram 620 indicates that, during a cardiac cycle, motion of the RV point is much less than motion of the LV point.

Further, data indicate that the RA point also tends to move much less than the LV point. Hence, length of the RA-to-RV segment of the triangle 610 varies less during a cardiac cycle than length of the RV-to-LV segment or the RA-to-LV segment. As described herein, by collecting data with respect to time, waveforms are generated that exhibit physiologic behavior. Such waveforms can be analyzed by one or more techniques where a result or results may be relied on for diagnosis, determining or selecting a configuration, etc.

As described herein, an exemplary method can include subtracting right ventricular position in a 3-D coordinate system from left ventricular position in the 3-D coordinate system, or vice versa, to remove from the analysis movement contributions caused by respiration, the heart itself or a combination of both respiration and the heart itself (e.g., movement of the heart in the body). Such a technique can also remove possible artifacts caused by body movements such as posture changes. In various scenarios, one or more subtraction techniques may be applied, for example, to isolate particular movement (e.g., consider a technique that subtracts contractile motion of a particular electrode). A centroid may also be calculated for various points (e.g., a centroid of a triangle defined by a RA electrode, a RV electrode and a LV electrode). In such an example, movement of the centroid may be tracked over time (e.g., as a centroid waveform) and analyzed to, for example, enhance diagnosis of cardiac condition or selection of a configuration (e.g., electrodes, timing parameters, etc.).

As shown in a block 632 of FIG. 6, for a site associated with the right ventricle, position of this site can be represented as $Site_{RV}=(X_{RV}, Y_{RV}, Z_{RV})$ and for a site associated with the left ventricle, position of this site can be represented as $Site_{LV}=(X_{LV}, Y_{LV}, Z_{LV})$. Given the foregoing notation, as shown in a block 634 of FIG. 6, a vector can be defined as $Vector_{RV-LV}=Site_{RV}-Site_{LV}$. As shown by the vector operations of a block 636 of FIG. 6, magnitude of this vector can be calculated as:

$$Mag_{RV-LV}=|Site_{RV}-Site_{LV}|=((X_{RV}-X_{LV})^2+(Y_{RV}-Y_{LV})^2+(Z_{RV}-Z_{LV})^2)^{0.5}$$

Also shown in the block 636, vector rotational angle can be calculated using the dot product of two vectors:

$$Vector_{RV-LV} \cdot Vector_{Ref}=|Vector_{RV-LV}||Vector_{Ref}|\cos \theta$$

In the foregoing equation, the arc cosine function provides the angle θ. As indicated in the block 636, angular velocity ω can be calculated from the time derivative of the angle (dθ/dt) and angular acceleration from the second time derivative of the angle (dω/dt). The various position data or angle data (or derivatives or other variants thereof), where available with respect to time, may be represented as waveforms. Such waveforms may be analyzed, for example, by comparing waveforms for different conditions (e.g., electrode configurations, stimulation parameters, patient positions, activity levels, etc.). Also in FIG. 6, a vector angles diagram 640 indicates angular movement of a RA-to-RV vector and a RA-to-LV vector during a cardiac cycle.

In the example of FIG. 6, the reference vector, $Vector_{Ref}$, is typically a fixed vector, for example, based on positions at a time of (or prior to) a ventricular stimulus (e.g., V-pacing) or an intrinsic ventricular event (e.g., R-sense) (e.g., to provide a baseline). As described herein, any time point or points may serve as a fiducial or fiducials in time, for example, with respect to the cardiac cycle. As explained with respect to FIG. 6, the vector RV-to-LV ($Vector_{RV-LV}$) is a changing vector that changes in response to contraction of the heart, whether caused by intrinsic activity or delivery of a stimulus (e.g., as associated with a pacing therapy).

As to an exemplary transform method, at each electrode, onset and end of ventricular systolic motion or electrical activation may be determined from an EGM signal (e.g., based on peak amplitude, peak negative slope, or achieving a threshold voltage or slope, among other techniques). The electrode positions at the time of activation and end of systolic motion may be noted. In this example, a transformation may occur through a series of rotation matrices. For example, change in vector magnitude along a single axis may be optimized (e.g., maximal RA-to-RV shortening as being along the Z-axis). In an alternative approach, the absolute maxima of a distance vector may be utilized to determine the cardiac axis.

Figure 7:
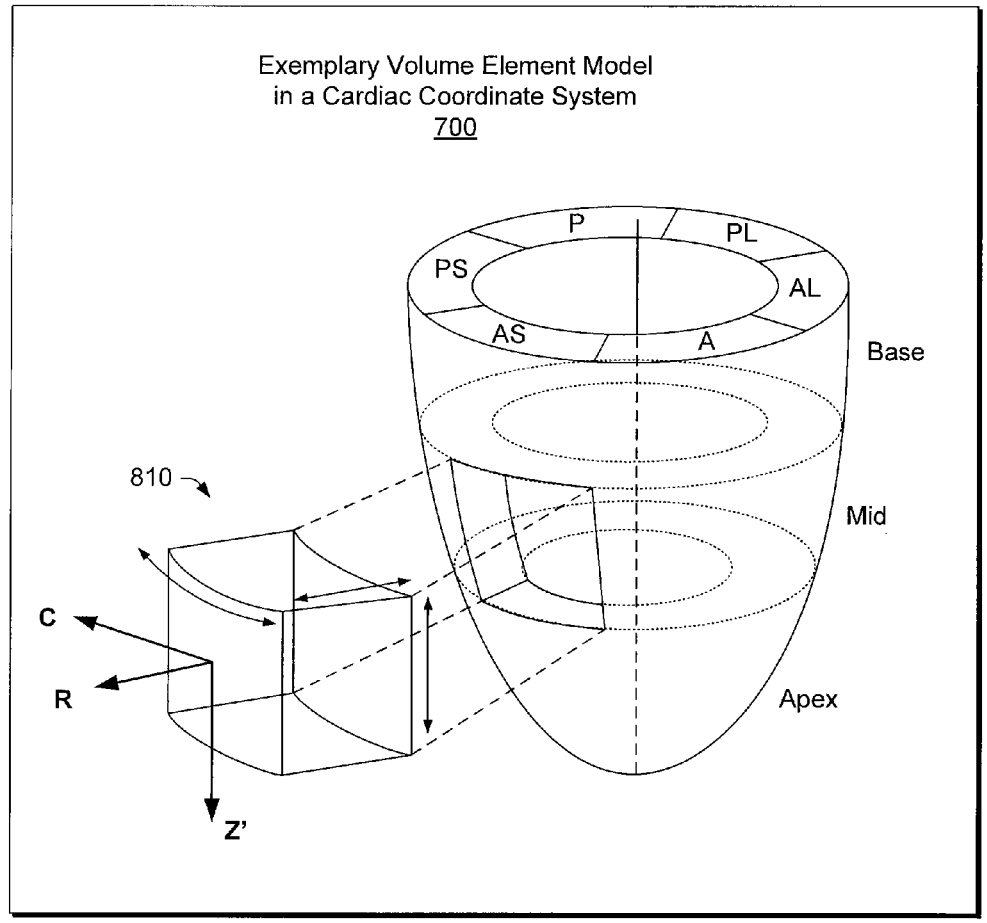
FIG. 7 is a diagram of a volume element model of the heart along with a block diagram of an exemplary method to define a cardiac coordinate system.
Figure 7:
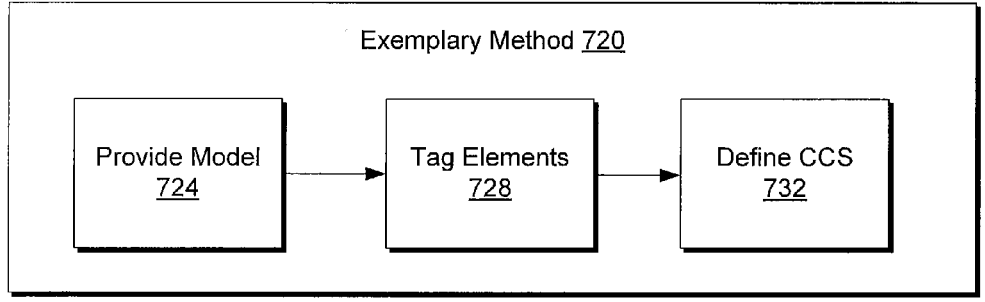

FIG. 7 shows an exemplary volume element model 700 and an exemplary method 720 for defining a cardiac coordinate system (CCS). The model 700 includes various volume elements 710 where each volume element corresponds to an angular segment and an axial segment of the heart. In the example of FIG. 7, the angular segments include posterior, posterior superior, posterior lateral (or posterolateral), anterior, anterior superior and anterior lateral (or anterolateral) while the axial segments include base, mid and apex. In the example of FIG. 7, each volume element can be described with respect to a cylindrical CCS with coordinates Z', R and C. Further, the collection of 16 volume elements defines a chamber volume for the left ventricle.

The exemplary method 720 includes providing a model 724, tagging multiple volume elements based on location of an electrode and defining a CCS 732 based on the tagged elements. For example, using a sectioned left ventricular model a clinician may estimate electrode placement locations under fluoroscopic guidance to define orientation of the model. Actual electrode locations may be provided in a naïve coordinate system associated with a localization system, referred to as "LPS", and notated:

$a_{x_{LPS}}, a_{y_{LPS}}, a_{z_{LPS}}$

In this example, the defined location on the left ventricular model would be $a_{x_{model}}, a_{y_{model}}, a_{z_{model}}$ By defining $a_{x_{LPS}}, a_{y_{LPS}}, a_{z_{LPS}} = a_{x_{mod\ el}}, a_{y_{mod\ el}}, a_{z_{mod\ el}}$ and solving for the inverse solution, one may calculate a rotation matrix to transform the model axes.

Figure 8:
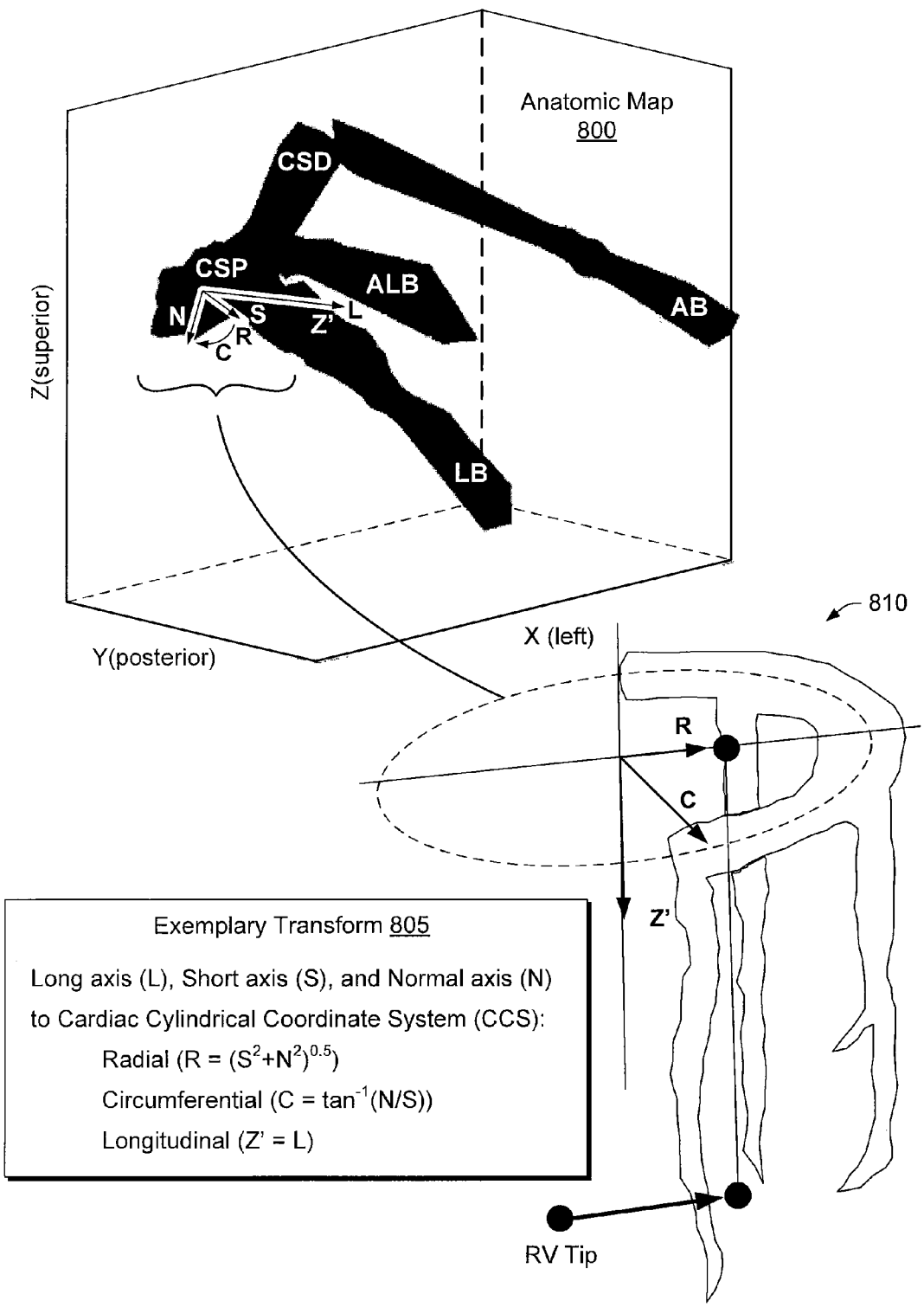
FIG. 8 is an anatomic map of a venous network of the heart and a diagram of a projection technique that can define a cardiac coordinate system.

FIG. 8 shows an anatomic map 800 of a venous network 810 where the map 800 was generated using ENSITE® NAVX® software based on position data acquired with respect to a naïve coordinate system (X, Y, Z). In this example, a data mapping procedure took less than 15 minutes, including access to three branches of the coronary sinus and construction of the anatomic map 800. After the mapping procedure, the catheter was removed, the LV lead was placed in a location at the implanting clinician's discretion (see anterolateral branch), and the device implant was completed.

FIG. 8 also shows an exemplary coordinate transformation 805. In this example, raw naïve Cartesian coordinates of the positions are shown with respect to the X, Y, Z coordinate system where X corresponds to "left", Y corresponds to "posterior" and Z corresponds to "superior". Another coordinate system is shown with respect to coordinates for a long axis (L), a short axis (S) and a normal axis (N). Yet another coordinate system is shown with respect to coordinates for a longitudinal axis (Z'), a radial dimension (R) and a circumferential dimension (C).

As described herein, a coordinate transform may transform coordinates associated with a localization system into one or more alternative coordinate systems. For the ENSITE® NAVX® localization system, X is from right to left, Y is from anterior to posterior, and Z is from inferior to superior in a Cartesian system that typically has an origin at the "belly patch" (see patch 428 of FIG. 4). In one alternative, motions can be resolved in a Cartesian coordinate system with the same principal directions but whose origin is located at a different location, for example one of the other surface patches, an intracardiac or other indwelling electrode, or some computed stable reference point within the body. In yet another alternative, a cardiac coordinate system may be computed in which the naïve Cartesian X, Y and Z directions correspond with a short axis (S), a normal axis (N), and along axis (L) of the heart. In FIG. 8, the exemplary coordinate transformation 805 corresponds to a cylindrical cardiac coordinate system that resolves 3-D motions to longitudinal (Z'), radial (R), and circumferential (C) components.

A coronary sinus projection transform technique is described with respect to the venous network 810 of FIG. 8, which shows a RV tip electrode location and an associated vector. According to this technique, during left ventricular (LV) lead implant, electrode location data may be collected and fitted to an elliptical/spherical basal model of the LV. Data collected along the atrioventricular groove from the entrance of the coronary sinus to the subselection of the lateral vein may be considered to be a quadrant of a symmetrical basal model for which a basal centroid may be defined. To determine the apical point a corrected right ventricular electrode location may be utilized as shown with respect to the venous network 810.

Figure 9:
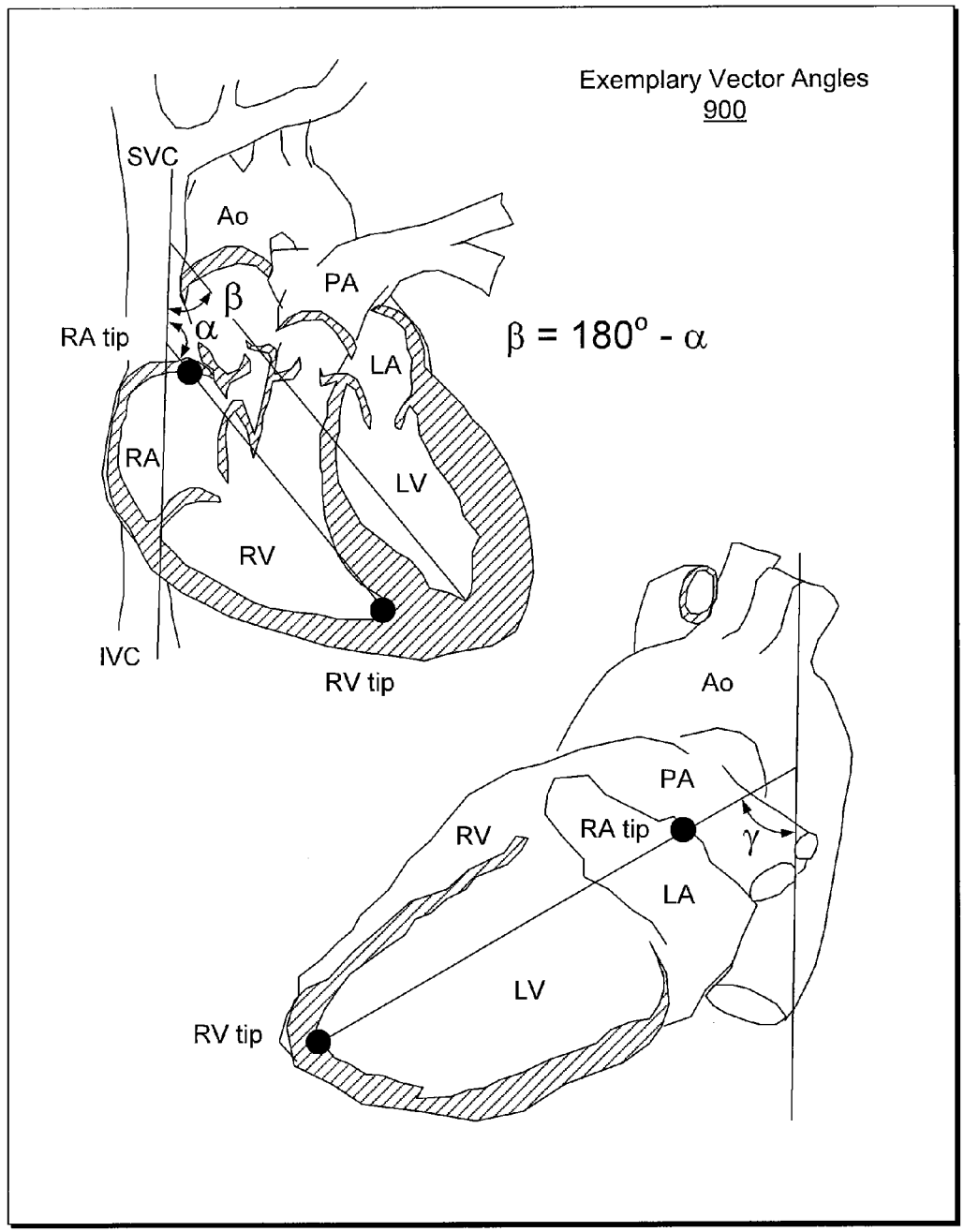
FIG. 9 is a diagram of cross-sections of the heart along with angles that can define a cardiac coordinate system.

FIG. 9 shows various diagrams of the heart 900 along with particular vector angles. In the example of FIG. 9, the superior vena cava (SVC) is considered to be anatomically vertical and therefore approximately parallel to the ENSITE® NAVX® Z-axis. Accordingly, positions of an electrode passing through the SVC may be recorded and relied on to establish a line parallel to the Z-axis. However, depending on patch placement (see FIG. 4) this parallelism may not be exact. To correct for such error, the ENSITE® NAVX® Z-axis can be rotated along the single axis to fit the data collected through the SVC. In addition to data collection along the passage through the SVC, a lead with a pair of electrodes incorporated proximally may also be used.

In the approach of FIG. 9, defined vertical axis angles of rotation may be derived using the lead locations in two planes (e.g., XY and XZ). Rotation angles may be estimated with the addition of correction factors to estimate two angles of rotation as shown in FIG. 9 and derivation of the cardiac axis may follow.

As described herein, the various vector metrics shown in FIG. 6 may be recast in a cardiac coordinate system (CCS). For example, the naïve coordinate system (NCS) with Cartesian coordinates X, Y, Z may be transformed via PCA to a cylindrical CCS with coordinate Z', R and C. Further, an exemplary method may compare data in a cylindrical CCS to vector data in, for example, a naïve Cartesian coordinate system.

Figure 10:
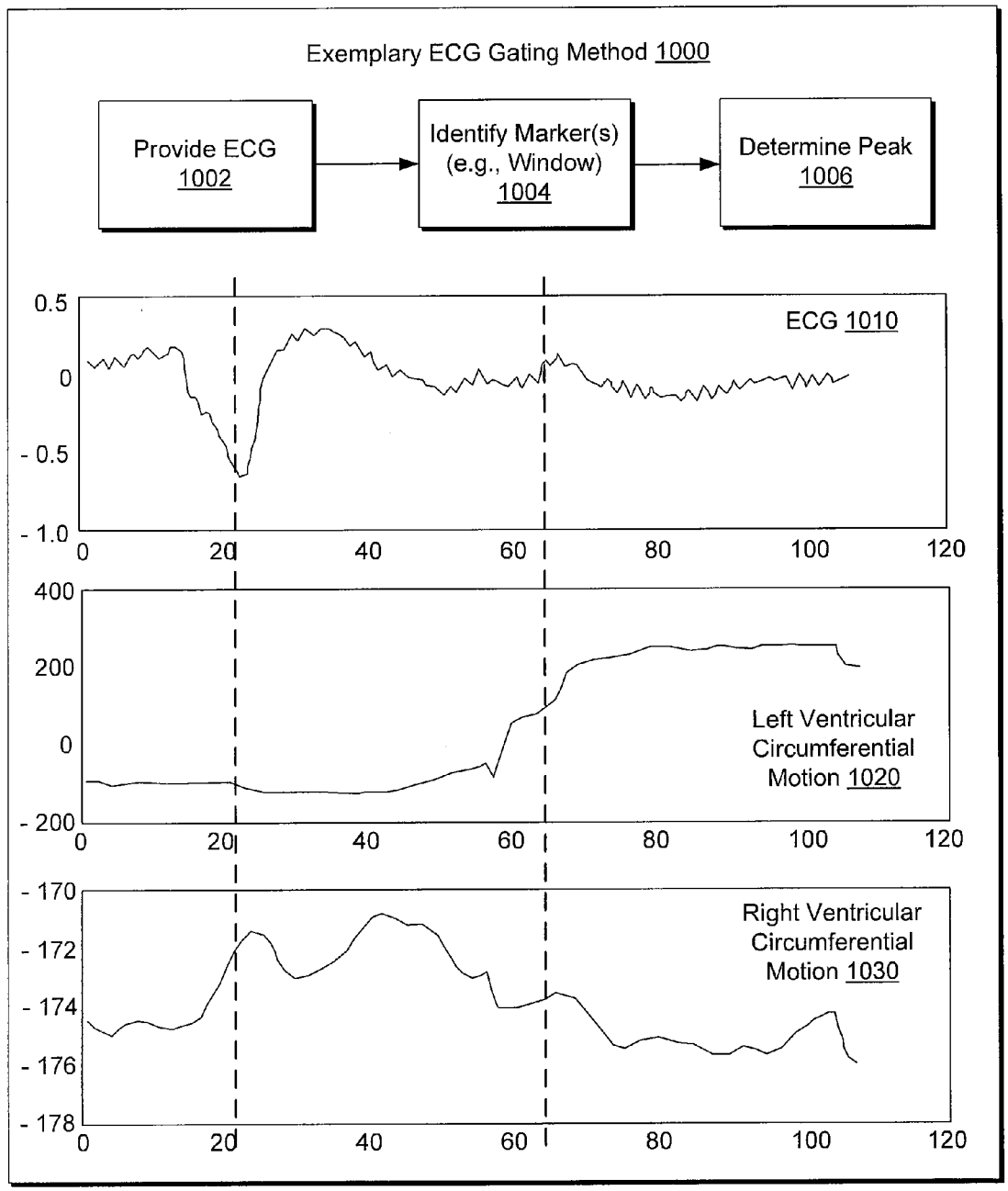
FIG. 10 is a block diagram of an exemplary method and a series of plots including a plot of electrical activity of the heart, left ventricular circumferential motion of the heart and right ventricular circumferential motion of the heart.

FIG. 10 shows an exemplary ECG gating method 1000 along with associated data plots 1010, 1020 and 1030. The method 1000 includes a provision block 1002 that provides an electrocardiogram (e.g., surface or IEGM). An identification block 1004 identifies one or more markers, for example, for a window. A determination block 1006, determines a time of peak motion based at least in part on one or more markers of the electrocardiogram. Accordingly, an exemplary method can include providing an electrocardiogram of a patient; providing position information with respect to time, the position information acquired via an electrode located in a venous network of the patient; defining a window based on the electrocardiogram; and analyzing the position information within the defined window to determine a time of peak motion of the electrode. In such a method, the analyzing can analyze the position information with respect to a cardiac coordinate system, which may be a cylindrical coordinate system. Such a method can enhance accuracy in determination of a time of peak motion of the electrode as being related to an intrinsic or paced activation of the heart. Time of peak motion may be used to adjust a cardiac therapy.

As described herein, an exemplary method may identifying motion due to respiration based on a predefined respiratory motion direction in a cardiac coordinate system. For example, such a method may include defining a respiratory motion direction by performing a principal component analysis. An analysis may include analyzing position information in a manner that accounts for respiratory motion (e.g., to select certain data, to discount or adjust certain motion, etc.). An exemplary method may include defining one or more windows based on an electrocardiogram and respiratory motion or respiratory motion alone.

As described herein, such an ECG gating technique can assist with data acquisition for purposes transforming data to a cardiac coordinate system (CCS). Dashed vertical lines indicate a time period from the Q-wave to the T-wave in the ECG plot 1010. These two cardiac events or features define a window in which peak points for different motion data signals (e.g., LV circumferential motion plot 1020 and RV circumferential motion plot 1030) were selected as CCS parameters.

In the example of FIG. 10, CCS-based parameters depend on selection of maximum/minimum (or "peak") points on motion waveforms such as the waveform plots 1020 and 1030. An electrode displacement signal of a localization system can sometimes be susceptible to a variety of factors (electrical artifact, noise issues, field inhomogeneities, etc.), which can cause irregular "bumps" in the signal. Such irregularities are counterintuitive and non-physiological in most cases. In addition, a transformation to CCS components has the potential to create some odd morphologies in a motion waveform. Occurrences of such morphologies can lead to improper selection of peaks in waveform, which may lead to inaccurate values for CCS parameters. A good amount of these false peaks were detected in the post-systolic time period. In an effort to limit suboptimal peak selections, CCS motion waveforms were ECG gated. As indicated in FIG. 10, peak selection was restricted to a window defined between the Q-wave and the onset of the T-wave.

Figure 11:
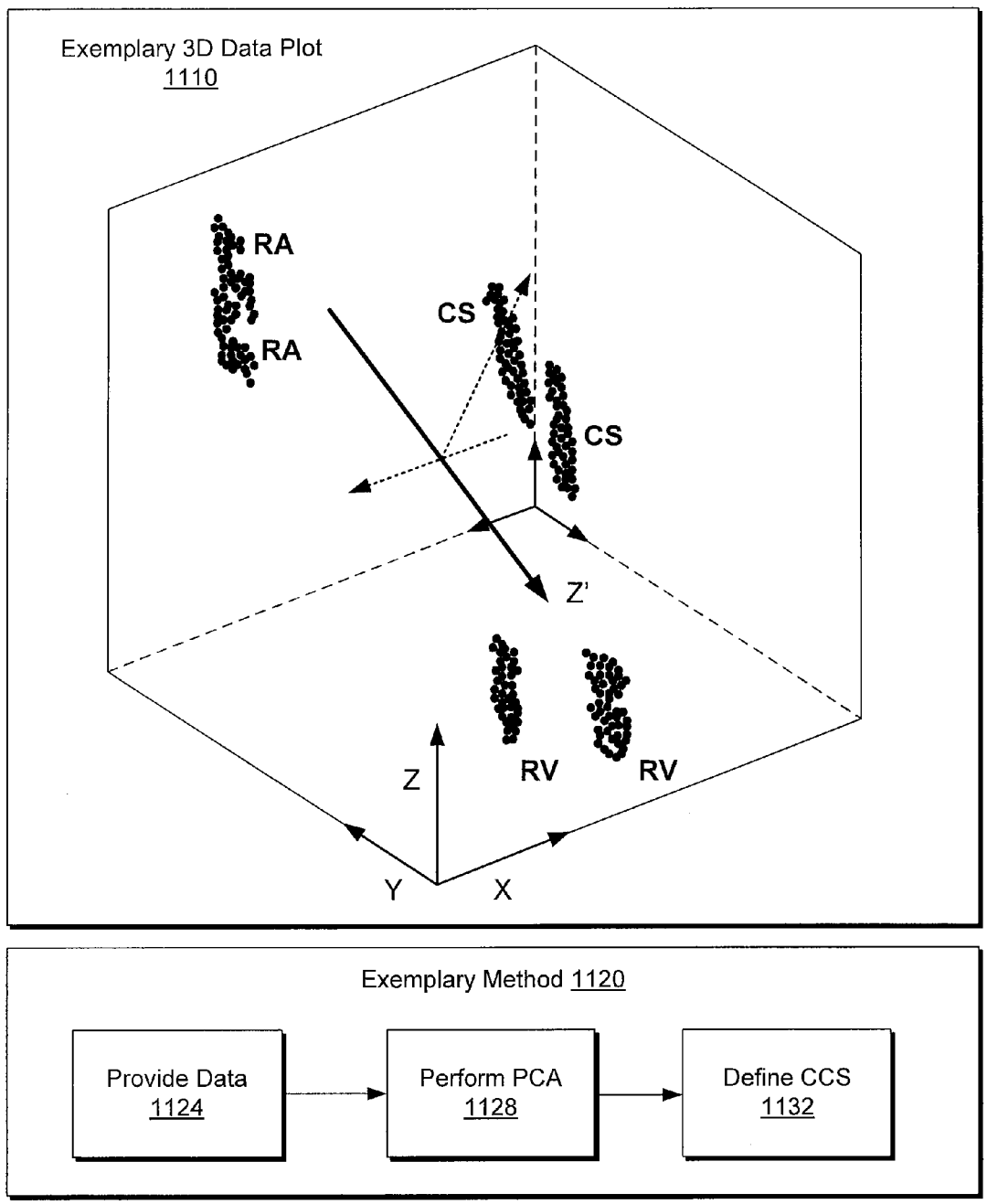
FIG. 11 is a 3-D plot of cardiac motion information and a block diagram of an exemplary method to define a cardiac coordinate system based on a principal component analysis (PCA).

FIG. 11 shows an exemplary plot 1110 of 3-D data acquired using a localization system and an exemplary method 1120 for defining a CCS. Specifically, the 3-D data are traces of electrode motion paths of individual electrodes positioned in a patient. The method 1120 includes providing data 1124, performing a PCA based on the provided data 1128, and defining a CCS based at least in part on the performed PCA. The plot 1110 shows 3-D data in a naïve X, Y, Z coordinate system and a new coordinate direction (e.g., Z'-axis) in a cardiac coordinate system. In the example of FIG. 11, the Z' direction corresponds to motion along a "long" axis of the heart.

Figure 12:
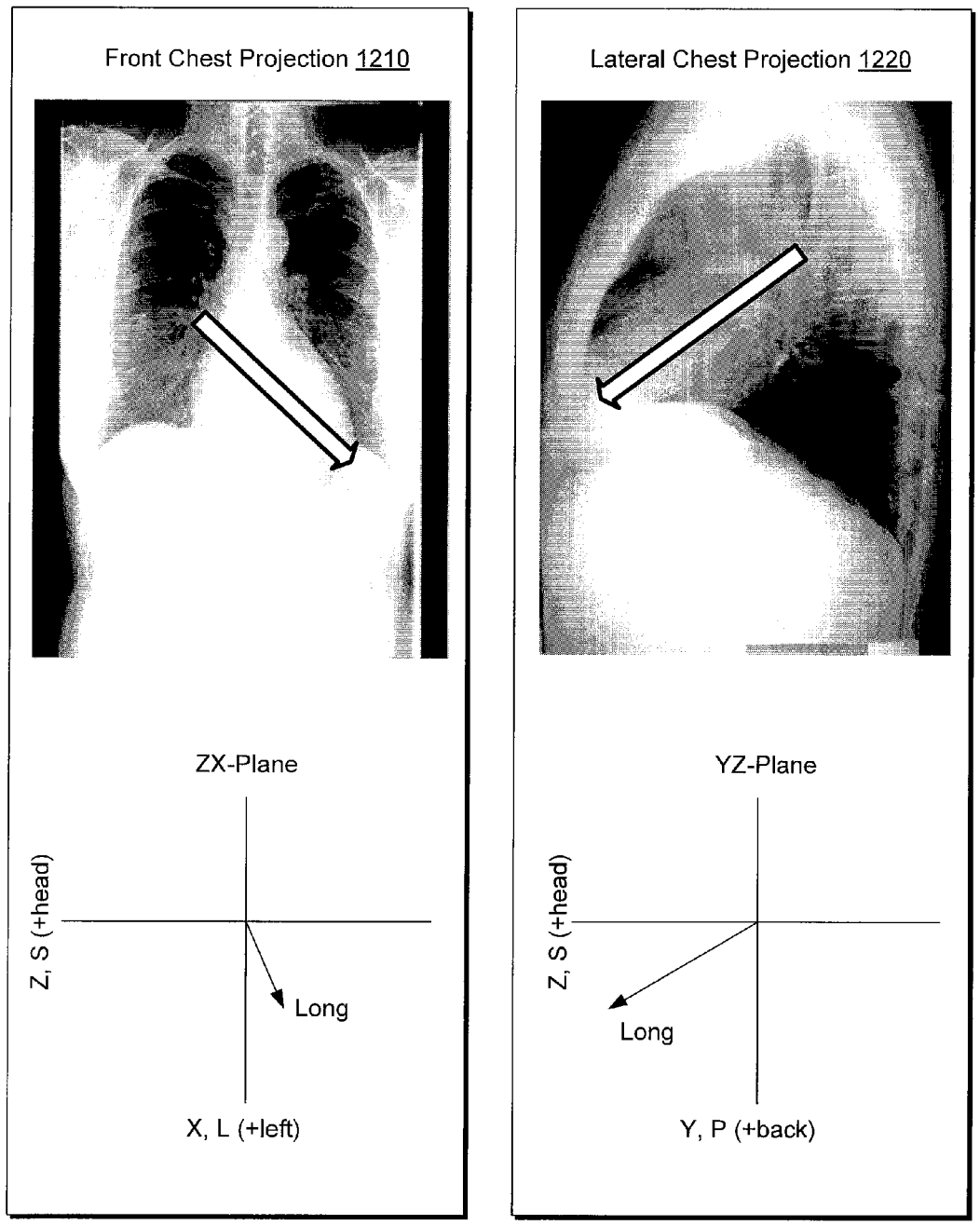
FIG. 12 is a series of X-rays of a patient along with an overlaid vector that represents a long axis of the heart.

FIG. 12 shows a 2-D X-ray front chest projection 1210 and a 2-D X-ray lateral chest projection 1220 along with an overlay of a PCA derived long axis vector. The front chest projection 1210 corresponds to a naïve coordinate system ZX plane while the lateral chest projection 1220 corresponds to the naïve coordinate system YZ plane.

Figure 13:
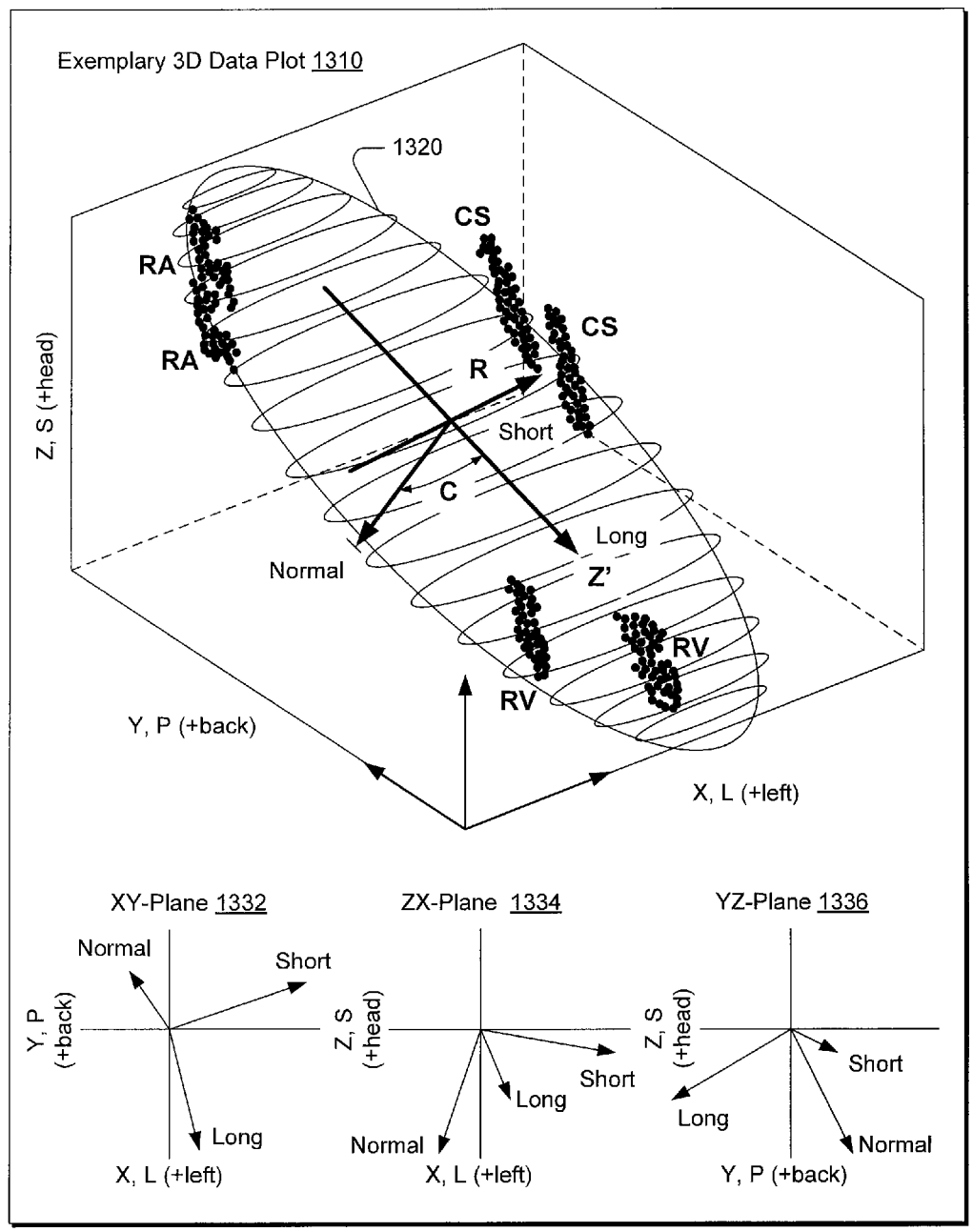
FIG. 13 is a series of plots of data with respect to various vectors.

FIG. 13 shows an exemplary 3-D plot 1310 with a prolate sheroid transform model 1320 along with projection plane plots 1332, 1334 and 1336. The plot 1310 and accompanying planar projections 1332, 1334 and 1336 include a long axis (L) and a short axis (S) as well as a normal vector (N). As described herein, once a PCA has been performed on electrode motion data and one or more resulting cardiac axes have been formed (e.g., L and S), the data can be transformed from the naïve coordinate system (e.g., X, Y, Z) to a cylindrical cardiac coordinate system (Z', R, C). Specifically, as indicated in the plot 325 of FIG. 3, the transformation can transform the long axis (L) to the Z' dimension, the short axis (S) to the radial dimension R and provides a circumferential angle C. Where data are recast simply to a Cartesian coordinate system (e.g., L, S, N), such a coordinate system may be referred to as a Cartesian cardiac coordinate system.

In the example of FIG. 13, the Z', R and C coordinates correspond to longitudinal, radial and circumferential motion, respectively. These are the primary directions in which myocytes of the heart shorten and elongate. Such a description of the mechanical behavior of the heart is in line with the standards in imaging and therefore easier to understand clinically, as well as physiologically (see, e.g., echocardiography of FIG. 5).

As described herein, a PCA can uncover a major axis that represents the long-axis of the LV, spanning from the center of the apex to the center of the base of the chamber. Further, a PCA can uncover a minor axis that represents the short-axis of the LV. A normal axis may be considered as being orthogonal to both the major and minor axes to provide a complete new 3-D coordinate system in the cardiac space.

In the plot 1310, the CCS axes produced for this particular patient appear to fairly accurate, anatomically, correspond to motion of the RA, RV, and LV (CS) electrode locations. The X-rays 1210, 1220 further confirm the PCA approach via 2-D projections of the CCS axes with sample chest X-rays from the patient, in the anterior-posterior (AP), or frontal, view 1210 and the lateral view 1220.

As mentioned, a prolate spheroid model approach may be applied as an alternative to PCA. Accordingly, a prolate spheroid model may be fit to data and then a coordinate system may be extracted from the fit model, for example, where a major axis of the prolate spheroid is considered a Z' axis and where a minor axis of the prolate spheroid is considered orthogonal to the Z' axis (see, e.g., R).

An exemplary method can include a PCA followed by fitting data to a prolate spheroid model. For example, a PCA can determine a Z' axis and the Z' axis may serve as a major axis of a prolate spheroid model. Such a method may optionally fit systolic data and diastolic data separately to provide two separate prolate spheroids (e.g., a systolic prolate spheroid and a diastolic prolate spheroid). In another example, data for specific points in time may be fit to construct a time varying prolate spheroid. Such a prolate spheroid may optionally be visualized to show variation during a cardiac cycle. Where data are acquired for intrinsic activation and paced activation of the heart, prolate spheroids for such activations may be compared to understand better efficacy of the paced activation. While intrinsic and paced activation are mentioned, other conditions may be varied to provide distinct prolate spheroids (or other models) that facilitate comparison of conditions.

As described herein, an exemplary method can include accessing cardiac information acquired via a catheter located at various positions in a venous network of a heart of a patient where the cardiac information includes position information with respect to time for one or more electrodes of the catheter; based on at least some of the position information, defining a cylindrical cardiac coordinate system; and defining a prolate spheroid in the cylindrical cardiac coordinate system where the prolate spheroid represents at least the left ventricle of the heart. In such a method, a PCA may help define a long axis of the prolate spheroid and a short axis of the prolate spheroid. In various methods, a prolate spheroid may be defined as a time varying prolate spheroid. In various methods, one prolate spheroid may correspond to a condition while another prolate spheroid corresponds to a different condition where, for example, comparing the two prolate spheroids can help assess left ventricular function for the conditions (e.g., intrinsic activation of the heart and paced activation of the heart or other conditions).

Figure 14:
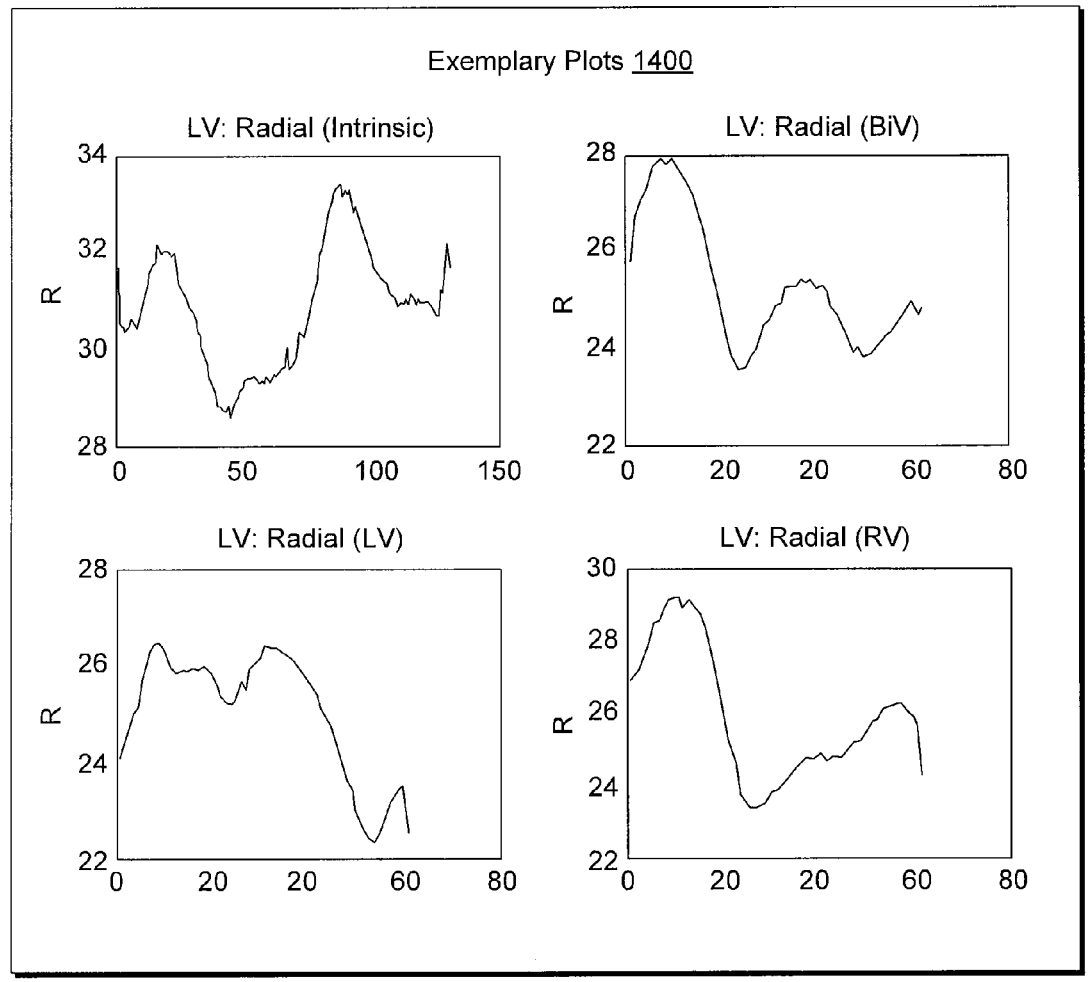
FIG. 14 is a series of radial motion data versus time for various conditions (i.e., intrinsic, right ventricular pacing, left ventricular pacing and biventricular pacing).
Figure 15:
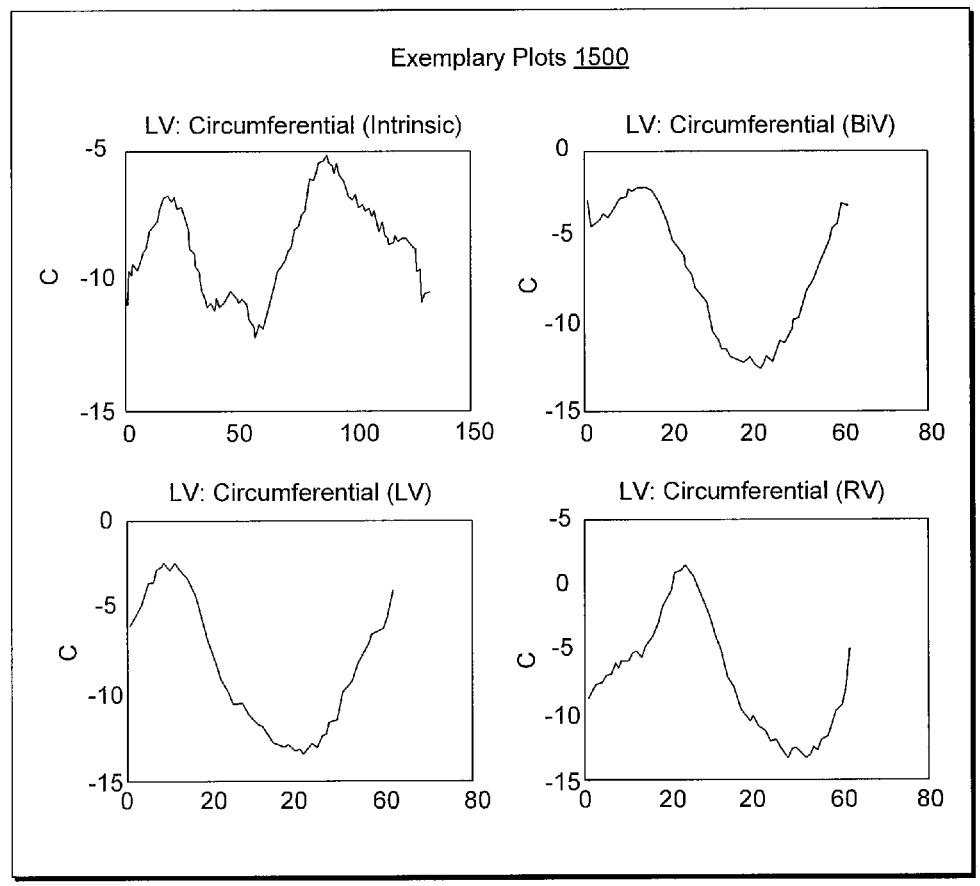
FIG. 15 is a series of circumferential motion data versus time for various conditions (i.e., intrinsic, right ventricular pacing, left ventricular pacing and biventricular pacing).
Figure 16:
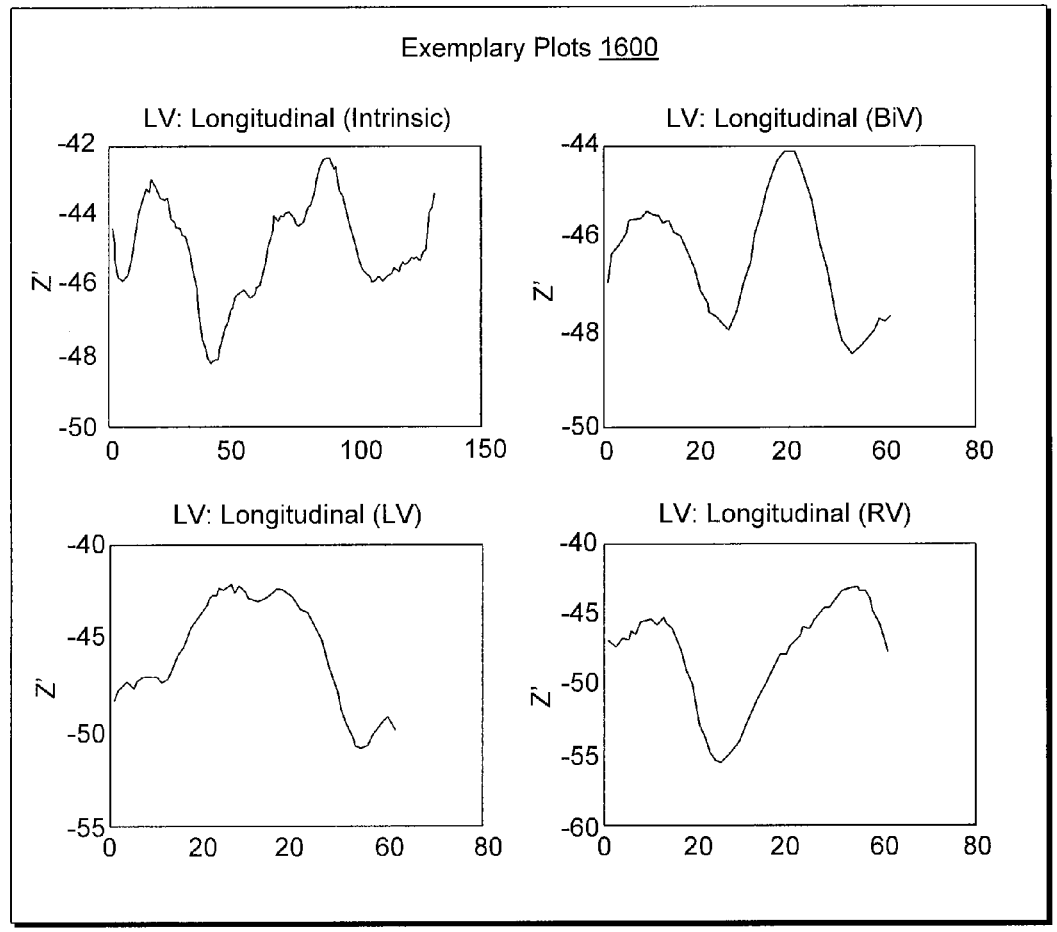
FIG. 16 is a series of longitudinal motion data versus time for various conditions (i.e., intrinsic, right ventricular pacing, left ventricular pacing and biventricular pacing).

FIGS. 14, 15 and 16 show motion waveform plots 1400, 1500 and 1600, respectively, for electrodes in a cardiac coordinate system. The plots 1400, 1500 and 1600 include data for intrinsic activation of the heart, right ventricular pacing, left ventricular pacing and biventricular pacing.

Specifically, FIG. 14 shows example single cardiac cycle waveforms of radial motion of LV distal electrode (R(t)), ensemble averaged over recorded segment; FIG. 15 shows example single cardiac cycle waveforms of circumferential motion of LV distal electrode (C(t)), ensemble averaged over recorded segment; and FIG. 16 shows example single cardiac cycle waveforms of longitudinal motion of LV distal electrode (Z'(t)); ensemble averaged over recorded segment.

Once some evidence to validate a PCA-based CCS has been acquired, a clinician may implement an exemplary method to transform acquired data from a naïve coordinate system (or Cartesian CCS (e.g., L, S, N)) to a cylindrical CCS (Z', R, C). For various examples described herein, the MATLAB® framework "cart2pol" function (The MathWorks, Inc., Natick, Mass.) can be used to perform a transformation to cylindrical coordinates. In addition, the angle C, for the circumferential coordinate, can be unwrapped to avoid $+/-\pi$ steps. A cylindrical CCS can yield electrode locations and displacements in radial, circumferential, longitudinal coordinates.

As to radial motion of the heart (see, e.g., the plots 1400 of FIG. 14), when viewing a cine of the heart over the course of the cardiac cycle, one may readily notice and appreciate motion radially going towards and away from the center of the chamber, especially in a short-axis view. Therefore, the radial component of myocardial motion is important and can be captured, to a certain degree, by the radial motion waveforms of the LV distal electrode. With R being the radial distance from the centroid, the systolic contraction appears to occur at a later time during LV only pacing, for a particular patient trial. Noting that peak-to-peak amplitudes, or the range of contractile movement, appear to be similar for all four modes of pacing/non-pacing for the particular patient.

As to circumferential motion of the heart (see, e.g., the plots 1500 of FIG. 15), with the majority of the myocyte fibers oriented in the circumferential direction, circumferential motion is arguably the primary and most meaningful component of myocardial motion. Circumferential motion accounts for the "twisting" and "untwisting" action seen in systole and diastole, respectively. For a particular patient both the BiV and LV only pacing interventions, which have been shown in studies to have common effects, increased the systolic peak-to-peak amplitude of circumferential motion. On the contrary, for the patient, RV pacing appeared to delay the contraction. Qualitatively, a smooth bell-shaped waveform from the BiV and LV plots could be observed and appreciated as an accurate reflection of the mechanical behavior of the myocardium.

As to longitudinal motion of the heart (see, e.g., the plots 1600 of FIG. 16), such motion can be observed in long-axis views, with the movement originating from the apex, propagating through the mid-ventricular region, and ending at the base. Longitudinal motion waveforms of the LV distal electrode for a particular patient were analyzed for intrinsic rhythm and the different pacing interventions performed during a clinical trial. Plotted data delineated the systolic phase in a LV only pacing, while, in contrast, RV pacing, which is known to induce acute intraventricular dyssynchrony, could be presumed in a RV only pacing plot, where evidence of dyskinetic motion in the longitudinal direction was shown (i.e., with the electrode moving towards the apex first, then towards the base).

A particular exemplary acquisition and analysis method includes inserting a catheter and moving the catheter from a proximal coronary sinus location to a distal coronary sinus location and to anterior, anterolateral, and lateral branches of the coronary sinus. At each location, the method includes recording about 10 seconds to about 30 seconds of data, including EGMs from each electrode at a frequency of 1200 Hz and including real-time position data for each electrode (e.g., X, Y, Z patch coordinate system) at a frequency of about 93 Hz (e.g., 1200/13 Hz). Additionally, at each location, the method includes sampling location points for a subsequent transformation process associated with a cardiac coordinate system. After the catheter-based procedure, the exemplary method includes inserting and placing a conventional LV bipolar lead targeted to a particular coronary sinus branch of the patient.

In an exemplary offline method, the structure and anatomy of the coronary sinus for a patient (along long, short, and normal axes) were analyzed based on data acquired during an intraoperative procedure. In this method, the short-normal plane was aligned with the coronary sinus proximal and distal direction (i.e. the base of the heart), the short axis was aligned pointing toward the RV tip electrode's projection onto the basal plane, and the long axis was aligned pointing toward the apex, in a direction approximately through the center of the basal plane. A cylindrical coordinate system was then computed using the long axis as the Z' direction, the short axis as the 0° for circumferential direction (C) and counterclockwise positive when looking base-to-apex, and radial direction (R) measured from the long axis outward (see, e.g., FIG. 8).

With respect to cardiac mechanics, mechanical coordination between the RV and LV, and more importantly across regions of the LV, is a major determinant of overall pump function. Preoperative echocardiography, including Tissue Doppler Imaging (TDI) (see Ansalone G, Giannantoni P, Ricci R, et al.: Doppler myocardial imaging to evaluate the effectiveness of pacing sites in patients receiving biventricular pacing. J Am Coll Cardiol 2002; 39:489-499) and its derivatives like Tissue Tracking Imaging (TTI) (see Pan C, Hoffmann R, Kühl H, et al.: Tissue tracking allows rapid and accurate visual evaluation of left ventricular function. Eur J Echocardiogr 2001; 2:197-202) and Tissue Synchronization Imaging (TSI) (see Murphy R T, Sigurdsson G, Mulamalla S, et al.: Tissue synchronization imaging and optimal left ventricular pacing site in cardiac resynchronization therapy. Am J Cardiol 2006; 97:1615-1621), or 2-D speckle tracking methods (see Leitman M, Lysyansky P, Sidenko S, et al.: Two-dimensional strain—A novel software for real-time quantitative echocardiographic assessment of myocardial function. J Am Soc Echocardiogr 2004; 17:1021-1029) can reveal regions of late mechanical activation or hypokinesis that negatively impact cardiac performance. However, echocardiography does not allow one to judge accessibility of these regions via the coronary veins. Further, TDI only gives longitudinal motion of myocardial segments in the apical view, and speckle tracking yields only 2-dimensional motion and strain information. Moreover, both of these techniques have been shown to have large inter-observer variability (Chung E S, Leon A R, Tayazzi L, et al.: Results of the predictors of response to CRT (PROSPECT) trial. Circ 2008; 117:2608-2616).

As described herein, a localization system (e.g., the ENSITE® NAVX® system) can record electrode motion in the coronary sinus and branches thereof by sampling at locations accessible by a guidewire or catheter. An exemplary method may target lead placement to a location directly measured to have mechanical latency. In addition to acquiring data of 3-D electrode displacement and velocity, as mentioned, projection of data onto computed cardiac axes allows the resolution of radial, circumferential, and longitudinal components of cardiac motion from a simultaneous acquisition. As described herein, an exemplary method can use localization system derived motion to generate waveforms reminiscent both of TDI long-axis velocity traces or TT long-axis displacement and of 2-D speckle tracking radial displacement or cardiac twist traces concurrently.

As to septal motion, an echocardiography parameter "Q to max posterior movement of septum" is an M-mode measurement that estimates the time from the onset of the Q-wave from the electrocardiogram (ECG) to peak of the signal waveform representing posterior movement of the septum. With respect to the transducer at the appropriate angle, this posterior movement of the septum corresponds to the single radial axis of motion in the M-mode echo.

To determine an analog to the echocardiography parameter "Q to max posterior movement of septum", a CCS parameter, "Q to peak septal motion", was developed, according to following equation:

$$Q \text{ to peak septal motion} = (\text{Time of peak radial motion of } RV \text{ tip electrode}) - (\text{Time of } Q\text{-wave})$$

In this exemplary approach, the RV tip electrode was thought to be the data point closest to representing the myocardial motion of the interventricular septum.

Figure 17:
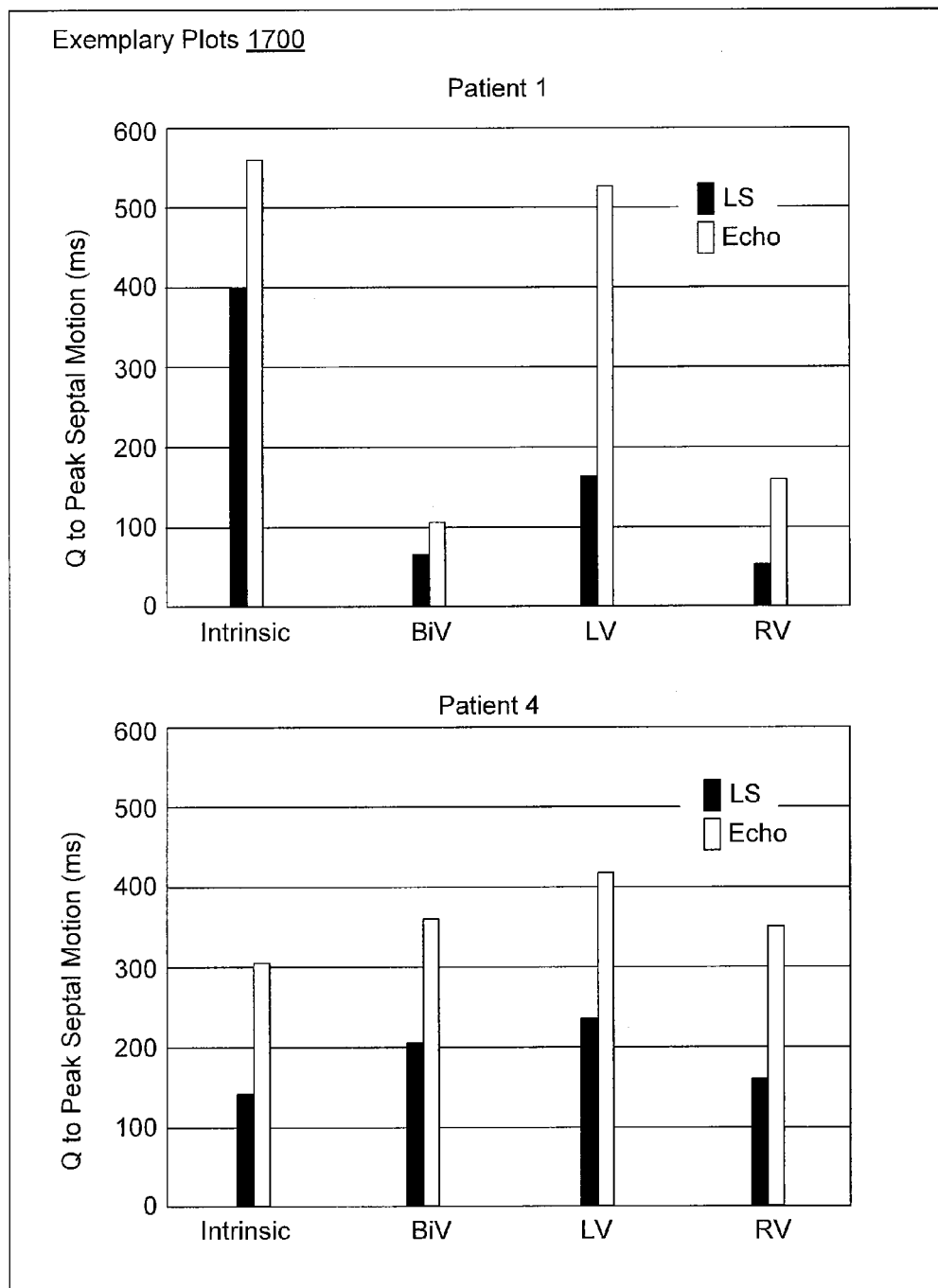
FIG. 17 is a series of plots for a septal motion parameter derived in a cardiac coordinate system and an analogous echocardiography parameter.

FIG. 17 shows exemplary plots 1700 that compare CCS based septal motion parameter and septal motion delay from echocardiography analysis for Patients 1 and 4 of a trial assessment. The plots 1700 show, for each patient, a comparison of the CCS Q-to-peak septal motion parameter with the time from Q to max posterior movement of septum as assessed by M-mode echocardiography assessment. The CCS septal motion parameter was based on the Q-wave detection and the peak selection from ECG-gated (Q-to-T wave) radial motion of LV electrodes (see, e.g., FIG. 10).

The plotted data for Patient 1 demonstrates a common trend between the CCS Septal Motion time delay parameter and the equivalent echo parameter, with respect to the various pacing interventions. The plotted data for Patient 4 also shows a strong correlation between the CCS parameter and the echocardiography parameter.

Figure 18:
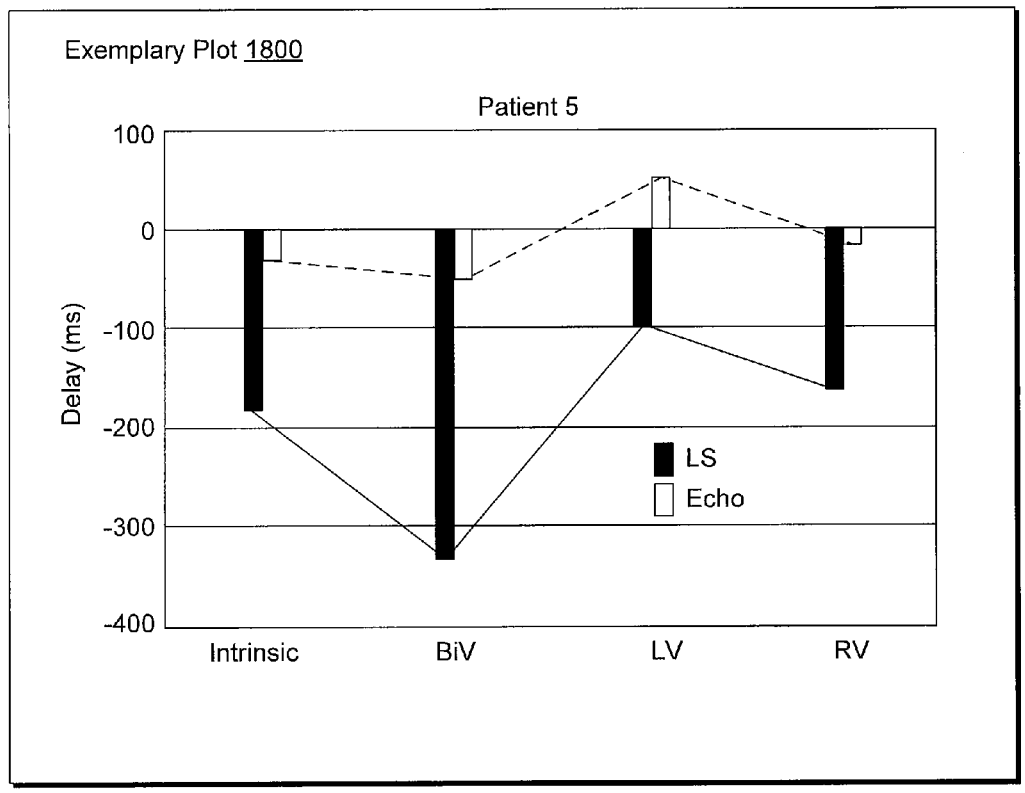
FIG. 18 is a plot of a dyssynchrony parameter derived in a cardiac coordinate system and an analogous echocardiography parameter.

FIG. 18 shows an exemplary plot 1800 for delay parameters. Specifically, the plot 1800 shows a comparison between a CCS-based dyssynchrony parameter and an "anferolateral-to-inferoseptal basal delay in peak velocity" from an echocardiography TDI analysis for Patient 5 of a trial assessment. In the plot 1800, the CCS-based dyssynchrony parameter was based on peak selections from ECG-gated (Q-to-T wave) circumferential motion of RV and LV electrodes (see, e.g., FIG. 10) and the echocardiography dyssynchrony parameter is the "anferolateral-to-inferoseptal basal delay in peak velocity" calculated from TDI, referred to simply as "Echo" in the plot 1800.

A common parameter to assess or describe cardiac mechanical properties in heart failure (e.g., for CRT candidates) is intraventricular dyssyncrhony. Specifically, the time delays to peak velocities of several different myocardial segments (in a standard 12-segment model) can be measured by echo tissue Doppler imaging (TDI). Once these time delays are obtained, other parameters, specifically the "anterolateral-to-inferoseptal basal delay in peak velocity" can be calculated. This septal-to-lateral delay is generally the standard for dyssynchrony, as it provides the temporal difference in mechanical activation from one wall of the LV to the opposite wall in the chamber, yielding usually the maximum delay.

While dyssynchrony parameters can be computed in a standard or naïve coordinate system (e.g., of the ENSITE® NAVX® system) using magnitude displacements of RV and LV electrodes, a CCS-based approach allows a dyssynchrony value to be derived from RV and LV motion along directions that are physiologically more meaningful and indicative of the tissue motion, rather than the electrode motion. An exemplary equation follows that was used to compute a CCS-based dyssynchrony parameter:

Delay=(Time to peak circumferential motion on $LV$ distal electrode)−(Time to peak circumferential motion on $RV$ distal electrode)

where, "+" sign=RV activated first, and "−" sign=LV activated first

Circumferential motion is shown in the foregoing equation by default, since the fibers in the midwall of the myocardium are oriented primarily in the circumferential direction. As described herein, as an alternative, longitudinal motion can be used, which may correlate better with the echo parameter (i.e., as it is based on the long-axis inherent in TDI).

Figure 19:
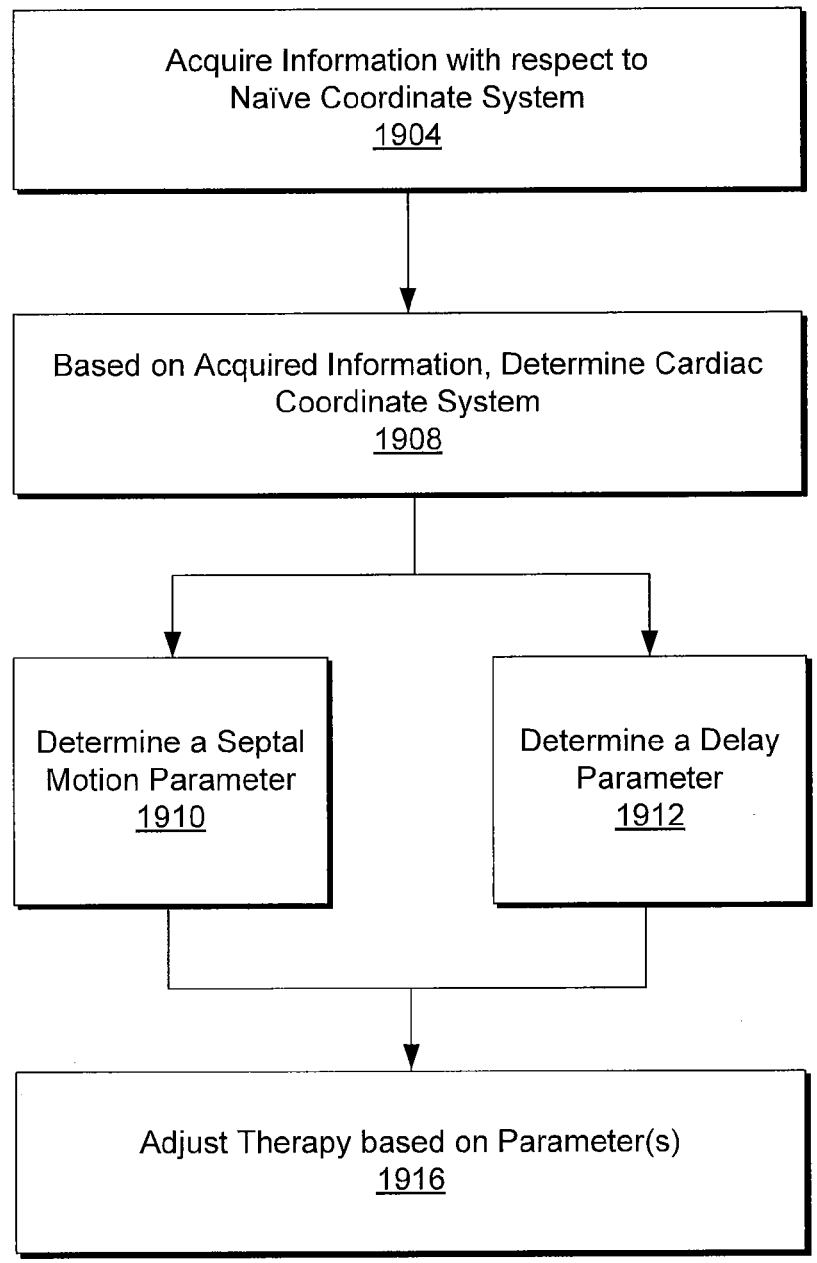
FIG. 19 is a block diagram of an exemplary method for determining one or more cardiac coordinate system-based parameters and adjusting a therapy based at least in part thereon.

FIG. 19 shows an exemplary method 1900 for adjusting a therapy based at least in part on a CCS-based parameter. The method 1900 includes an acquisition block 1904 that acquires information with respect to a naïve coordinate system. In a determination block 1908, the method 1900 determines a cardiac coordinate system based at least in part on the acquired information. In one or more subsequent determination blocks 1910, 1912, the method 1900 determines one or more parameters, which may be analogs to echocardiography or other conventional cardiac assessment parameters. In an adjustment block 1916, the method 1900 adjusts a therapy based at least in part on a determined parameter. In the example of FIG. 19, the septal parameter of block 1910 may be determined based on the foregoing Q to peak septal motion equation and the delay parameter of block 1912 may be determined based on the foregoing dyssynchrony (delay) parameter.

As described herein, an exemplary method that includes transforming localization system data into cylindrical coordinates provides a more accurate and intuitive method of analyzing and representing the localization system data. In addition, this data is more representative to the current clinical standard for measuring hemodynamic function and mechanical motion of the heart; echocardiography outside of cardiac MRI which has a number of inherent limitations including low frame rate acquisition, high cost, time consuming, and complex analysis.

As described herein, comparable analysis that may be developed using the transformed cardiac coordinate data includes M-mode, TDI and speckle tracking. TDI measures regional wall motion velocities along a longitudinal axis and speckle tracking which selects point locations of myocardium to track from frame to frame to evaluate strain, strain rate, tissue velocity, and LV rotation.

While using purely native localization system derived data may be appropriate when analyzing any Euclidean distance between two points, it is does not allow analysis of data in terms of component based analysis (motion along any independent X, Y, or Z axis or corresponding planes).

As described herein, an exemplary method of validating localization system data derived cardiac performance indices (e.g., metrics) by reference to comparable echocardiographic parameters includes transforming the localization system data to projections onto a specific axis or plane, as associated with an echocardiographic system. Physicians are accustomed to visualizing the heart in short-axis and long-axis when considering heart motion. Accordingly, transforming localization system acquired motion data to a CCS will facilitate interpretation and provide for quicker adaptation of techniques presented herein (e.g., a format familiar to physicians currently using other imaging modalities, such as echocardiography). A particular CCS provides relevance to the localization system motion data with respect to different directions and a physiological reference for analysis is provided by transforming the data into cylindrical coordinates (i.e., a coordinate system that corresponds physiologically to the orientation of ventricular fibers and mechanics).

As to transformation of coordinates, a series of rotation matrices can be used that affect vector magnitude along a single axis, which may be optimized (e.g., maximal RA–RV shortening along the z axis). In another approach, absolute maxima of a distance vector may be utilized to determine a cardiac axis. A particular exemplary approach uses principle component analysis (PCA), which can rely on variations in all electrode motions to determine cardiac axes. For example, the axis in which the greatest amount of variation is found can be defined as the long axis (primary contraction mechanism), the axis in which the second greatest amount of variation is found can be defined as the short axis (secondary contraction mechanism), and the axis in which the third greatest amount of variation is found can be defined as the normal axis (tertiary contraction mechanism). Such an approach was applied to acquired motion data to generate the L, S, N axes shown in FIGS. 8 and 13.

An exemplary approach can include location tagging, for example, where by a sectioned left ventricular model, the physician is able to estimate electrode placement locations under fluoroscopic guidance in order to define the orientation of the model. An exemplary approach can include coronary sinus projection. For example, during left ventricular (LV) lead implant, electrode location data may be collected and fitted to an elliptical/spherical basal model of the LV. An exemplary approach may rely on vector angles, for example, determined based on the superior vena cava (SVC) being considered as defining an axis.

While various examples described here rely, at present, on export and post-processing of data associated with location, an exemplary software program loaded into a localization system can enable such maps to be generated in near real-time (e.g., depending on memory, processors, etc.). An exemplary mapping module may be integrated fully into the ENSITE® NAVX® system in the same manner of other currently available maps (LAT, Peak Voltage, CFE, etc). Further, while the ENSITE® NAVX® system is currently configured as a product with a cart containing amplifiers and patient connections and another cart containing a workstation and software, the technology may be packaged differently, for example as a smaller (8-16 channel, versus the current 64 channel) amplifier rack built in to a laptop or programmer-like computer with appropriate software. Thus it becomes feasible to use such a system in real-time during CRT implant on a routine basis.

As mentioned, an exemplary method may include determining one or more distances (e.g., distance metrics) in an exemplary cardiac coordinate system (CCS). For example, a method may include mapping distance metrics based at least in part on distances between the various locations and an anatomical feature. In this example, the anatomical feature may be a feature of the heart such as, but not limited to, the right atrium, the right ventricle, the ostium of the coronary sinus, a valve of the heart, the apex of the heart and the base of the heart. In another example, an anatomical feature may be a nerve, such as, but not limited to, a phrenic nerve (e.g., to avoid phrenic nerve stimulation or to optionally stimulate the phrenic nerve, for example, as part of a respiratory therapy such as a sleep apnea therapy).

As described herein, various exemplary methods may be optionally performed using a robotic system. For example, a robotic system may be programmed with a score model and a list of parameters or conditions to vary as well as a number of sites to investigate. To initiate the robotic exploration, a clinician may position a lead in a tributary and then allow the robotic system to maneuver the lead (e.g., a few centimeters) forward, backward, etc., until it determines an optimal site. Depending on the number of sites investigated and variation in parameters or conditions, such a process may be performed in a matter of minutes. For example, where four sites are investigated in a selected vein and tested with intrinsic and paced activation, the latter for three VV delays, with 10 acquisitions per variation, for a heart rate of about 60 bpm, acquisition and analysis for the 16 combinations of the process may take around 5 minutes. As described herein, the exemplary external programmer of FIG. 20 optionally includes a robotic mechanism to maneuver a lead in a vein and associated exemplary control logic to perform an acquisition and analysis process to arrive at an optimal site.

Further details on vector-magnitude based metrics are provided in U.S. patent application Ser. No. 12/621,373 (assigned in its entirety to Pacesetter, Inc.), titled "Cardiac Resynchronization Therapy Optimization Using Vector Measurements Obtained from Realtime Electrode Position Tracking," the disclosure of which is hereby incorporated by reference.

Further details on area based metrics and volume based metrics are provided in U.S. patent application Ser. No. 12/398,460 (assigned in its entirety to Pacesetter, Inc.), titled "Cardiac Resynchronization Therapy Optimization Using Parameter Estimation from Realtime Electrode Motion Tracking," the disclosure of which is hereby incorporated by reference.

Further details on mechanical dyssynchrony based metrics are provided in U.S. patent application Ser. No. 12/476,043 (assigned in its entirety to Pacesetter, Inc.), titled "Cardiac Resynchronization Therapy Optimization Using Mechanical Dyssynchrony and Shortening Parameters from Realtime Electrode Motion Tracking," the disclosure of which is hereby incorporated by reference.

Further details on electrical and mechanical activation based metrics are provided in U.S. patent application Ser. No. 12/416,771 (assigned in its entirety to Pacesetter, Inc.), titled "Cardiac Resynchronization Therapy Optimization Using Electromechanical Delay from Realtime Electrode Motion Tracking," the disclosure of which is hereby incorporated by reference.

Details on IEGM metrics corresponding to myocardial infarction and scarring are provided in U.S. patent application Ser. No. 12/639,788 (assigned in its entirety to Pacesetter, Inc.), titled "Methods to Identify Damaged or Scarred Tissue Based on Position Information and Physiological Information," the disclosure of which is hereby incorporated by reference.

Details on energy drain metrics corresponding to myocardial infarction and scarring are provided in U.S. patent application Ser. No. 12/553,413 (assigned in its entirety to Pacesetter, Inc.), titled "Pacing, Sensing and Other Parameter Maps Based on Localization System Data," the disclosure of which is hereby incorporated by reference.

Details on stability metrics corresponding to myocardial infarction and scarring are provided in U.S. patent application Ser. No. 12/562,003 (assigned in its entirety to Pacesetter, Inc.), titled "Electrode and Lead Stability Indexes and Stability Maps Based on Localization System Data," the disclosure of which is hereby incorporated by reference.

Exemplary External Programmer

Figure 20:
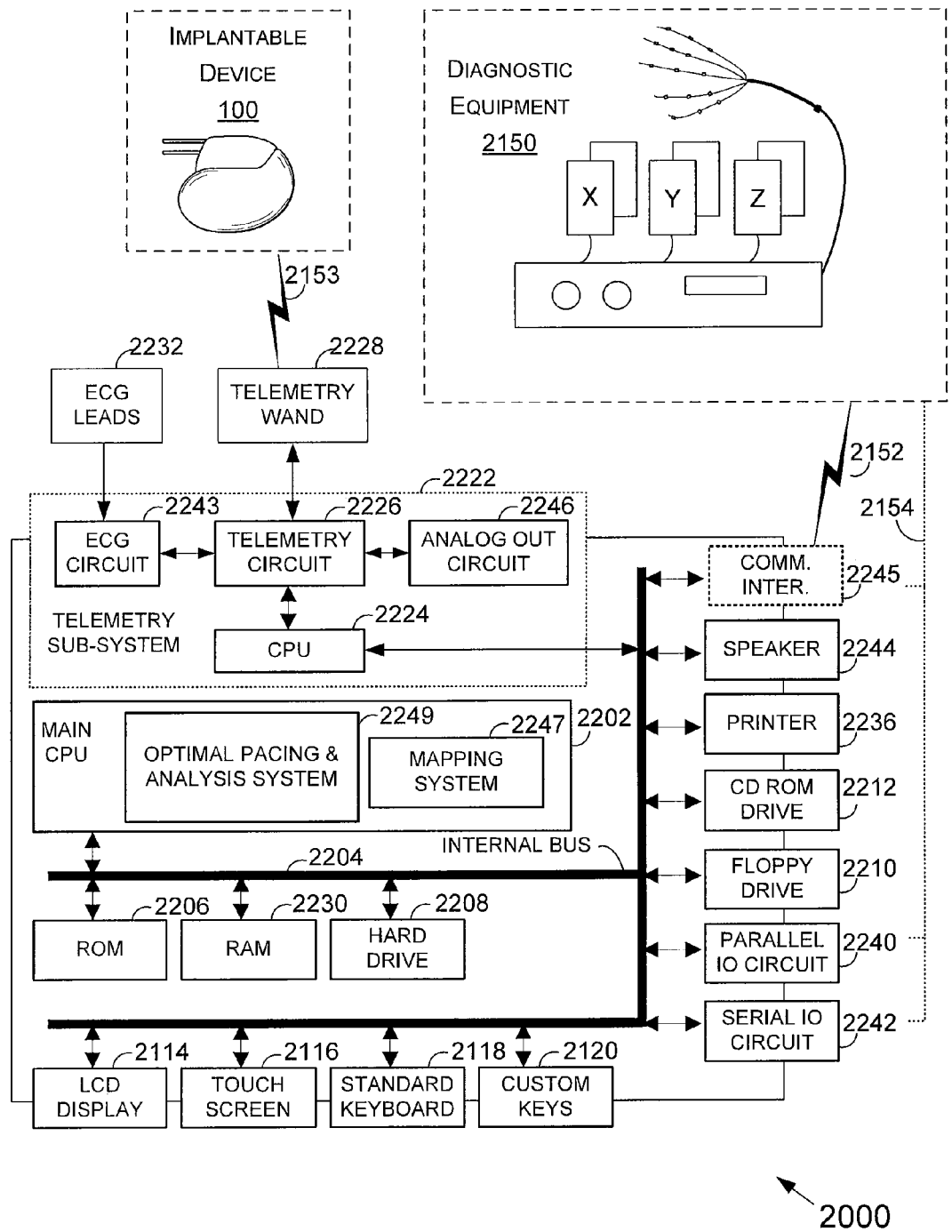
FIG. 20 is a diagram of an exemplary system for acquiring information and analyzing such information.

FIG. 20 illustrates pertinent components of an external programmer 2000 for use in programming an implantable medical device 100 (see, e.g., FIGS. 1 and 2). The external programmer 2000 optionally receives information from other diagnostic equipment 2150, which may be a computing device capable of acquiring motion information related to cardiac mechanics. For example, the equipment 2150 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 2000 in distinguishing respiratory motion from cardiac.

Briefly, the programmer 2000 permits a clinician or other user to program the operation of the implanted device 100 and to retrieve and display information received from the implanted device 100 such as IEGM data and device diagnostic data. Where the device 100 includes a module such as the position/metrics module 239, then the programmer 2000 may instruct the device 100 to measure potentials associated with position or to determine metrics and to communicate such information to the programmer via a communication link 2153. The programmer 2000 may also instruct a device or diagnostic equipment to deliver current to generate one or more potential fields within a patient's body where the implantable device 100 may be capable of measuring potentials associated with the field(s).

The external programmer 2000 may be configured to receive and display ECG data from separate external ECG leads 2232 that may be attached to the patient. The programmer 2000 optionally receives ECG information from an ECG unit external to the programmer 2000. The programmer 2000 may use techniques to account for respiration.

Depending upon the specific programming, the external programmer 2000 may also be capable of processing and analyzing data received from the implanted device 100 and from ECG leads 2232 to, for example, render diagnosis as to medical conditions of the patient or to the operations of the implanted device 100. As noted, the programmer 2000 is also configured to receive data representative of conduction time delays from the atria to the ventricles and to determine, therefrom, an optimal or preferred configuration for pacing. Further, the programmer 2000 may receive information such as ECG information, IEGM information, information from diagnostic equipment, etc., and determine one or more metrics for optimizing therapy.

Considering the components of programmer 2000, operations of the programmer are controlled by a CPU 2202, which may be a generally programmable microprocessor or microcontroller or may be a dedicated processing device such as an application specific integrated circuit (ASIC) or the like. Software instructions to be performed by the CPU 2202 are accessed via an internal bus 2204 from a read only memory (ROM) 2206 and random access memory 2230. Additional software may be accessed from a hard drive 2208, floppy drive 2210, and CD ROM drive 2212, or other suitable permanent or removable mass storage device. Depending upon the specific implementation, a basic input output system (BIOS) is retrieved from the ROM 2206 by CPU 2202 at power up. Based upon instructions provided in the BIOS, the CPU 2202 "boots up" the overall system in accordance with well-established computer processing techniques.

Once operating, the CPU 2202 displays a menu of programming options to the user via an LCD display 2114 or other suitable computer display device. To this end, the CPU 2202 may, for example, display a menu of specific programming parameters of the implanted device 100 to be programmed or may display a menu of types of diagnostic data to be retrieved and displayed. In response thereto, the clinician enters various commands via either a touch screen 2116 overlaid on the LCD display or through a standard keyboard 2118 supplemented by additional custom keys 2120, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to mapping of metrics (e.g., for patterns of conduction), the CPU 2202 includes a 3-D mapping system 2247 and an associated data analysis system 2249. The systems 2247 and 2249 may receive position information and physiological information from the implantable device 100 and/or diagnostic equipment 2150. The data analysis system 2249 optionally includes control logic to associate information and to make one or more conclusions based on metrics, for example, for planning an implant procedure or, more generally, to optimize delivery of therapy (e.g., to optimize a pacing configuration). The system 2247 and 2249 may include features for analyzing information to define a cardiac coordinate system (see, e.g., the method 300 of FIG. 3).

Where information is received from the implanted device 100, a telemetry wand 2228 may be used. Other forms of wireless communication exist as well as forms of communication where the body is used as a "wire" to communicate information from the implantable device 100 to the programmer 2000.

If information is received directly from diagnostic equipment 2150, any appropriate input may be used, such as parallel 10 circuit 2240 or serial 10 circuit 2242. Motion information received via the device 100 or via other diagnostic equipment 2150 may be analyzed using the mapping system 2247. In particular, the mapping system 2247 (e.g., control logic) may identify positions within the body of a patient and associate such positions with one or more electrodes where such electrodes may be capable of delivering stimulation energy to the heart, performing other actions or be associated with one or more sensors.

A communication interface 2245 optionally allows for wired or wireless communication with diagnostic equipment 2150 or other equipment (e.g., equipment to ablate or otherwise treat a patient). The communication interface 2245 may be a network interface connected to a network (e.g., intranet, Internet, etc.).

A map or model of cardiac information may be displayed using display 2114 based, in part, on 3-D heart information and optionally 3-D torso information that facilitates interpretation of information. Such 3-D information may be input via ports 2240, 2242, 2245 from, for example, a database, a 3-D imaging system, a 3-D location digitizing apparatus (e.g., stereotactic localization system with sensors and/or probes) capable of digitizing the 3-D location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 2000 optionally records procedures and allows for playback (e.g., for subsequent review). For example, a heart map and all of the electrical activation data, mechanical activation data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 2222 may include its own separate CPU 2224 for coordinating the operations of the telemetry subsystem. In a dual CPU system, the main CPU 2202 of programmer communicates with telemetry subsystem CPU 2224 via internal bus 2204. Telemetry subsystem additionally includes a telemetry circuit 2226 connected to telemetry wand 2228, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 2000 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 2000 (e.g., within a random access memory (RAM) 2230, hard drive 2208, within a floppy diskette placed within floppy drive 2210). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 2000 has a communication link to an external storage device or network storage device, then information may be stored in such a manner (e.g., on-site database, off-site database, etc.). The programmer 2000 optionally receives data from such storage devices.

A typical procedure may include transferring all patient and device diagnostic data stored in an implanted device 100 to the programmer 2000. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 2222 receives ECG signals from ECG leads 2232 via an ECG processing circuit 2234. As with data retrieved from the implanted device 100, signals received from the ECG leads are stored within one or more of the storage devices of the programmer 2000. Typically, ECG leads output analog electrical signals representative of the ECG. Accordingly, ECG circuit 2234 includes analog to digital conversion circuitry for converting the signals to digital data appropriate for further processing within programmer 2000. Depending upon the implementation, the ECG circuit 2243 may be configured to convert the analog signals into event record data for ease of processing along with the event record data retrieved from the implanted device. Typically, signals received from the ECG leads 2232 are received and processed in real time.

Thus, the programmer 2000 is configured to receive data from a variety of sources such as, but not limited to, the implanted device 100, the diagnostic equipment 2150 and directly or indirectly via external ECG leads (e.g., subsystem 2222 or external ECG system). The diagnostic equipment 2150 includes wired 2154 and/or wireless capabilities 2152 which optionally operate via a network that includes the programmer 2000 and the diagnostic equipment 2150 or data storage associated with the diagnostic equipment 2150.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 2202, the programming commands are converted to specific programming parameters for transmission to the implanted device 100 via telemetry wand 2228 to thereby reprogram the implanted device 100 or other devices, as appropriate.

Prior to reprogramming specific parameters, the clinician may control the external programmer 2000 to display any or all of the data retrieved from the implanted device 100, from the ECG leads 2232, including displays of ECGs, IEGMs, statistical patient information (e.g., via a database or other source), diagnostic equipment 2150, etc. Any or all of the information displayed by programmer may also be printed using a printer 2236.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 2000 optionally includes a modem to permit direct transmission of data to other programmers via the public switched telephone network (PSTN) or other interconnection line, such as a T1 line or fiber optic cable. Depending upon the implementation, the modem may be connected directly to internal bus 2204 may be connected to the internal bus via either a parallel port 2240 or a serial port 2242.

Other peripheral devices may be connected to the external programmer via the parallel port 2240, the serial port 2242, the communication interface 2245, etc. Although one of each is shown, a plurality of input output (IO) ports might be provided. A speaker 2244 is included for providing audible tones to the user, such as a warning beep in the event improper input is provided by the clinician. Telemetry subsystem 2222 additionally includes an analog output circuit 2246 for controlling the transmission of analog output signals, such as IEGM signals output to an ECG machine or chart recorder.

With the programmer 2000 configured as shown, a clinician or other user operating the external programmer is capable of retrieving, processing and displaying a wide range of information received from the ECG leads 2232, from the implanted device 100, the diagnostic equipment 2150, etc., and to reprogram the implanted device 100 or other implanted devices if needed. The descriptions provided herein with respect to FIG. 20 are intended merely to provide an overview of the operation of programmer and are not intended to describe in detail every feature of the hardware and software of the device and is not intended to provide an exhaustive list of the functions performed by the device 2000. Other devices, particularly computing devices, may be used.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
providing an electrocardiogram of a patient;
providing position information with respect to time, the position information acquired via an electrode located in a venous network of the patient;
defining a window based on the electrocardiogram; and
analyzing the position information within the defined window to determine a time of peak motion of the electrode wherein the analyzing analyzes the position information with respect to a cardiac coordinate system.

2. The method of claim 1 wherein the cardiac coordinate system comprises a cylindrical coordinate system.

3. The method of claim 1 wherein the cardiac coordinate system comprises a cardiac coordinate system defined at least in part by at least some of the position information.

4. The method of claim 3 wherein the cardiac coordinate system comprises a cardiac coordinate system defined at least in part by one or more of a principal component analysis and a prolate spheroid model.

5. The method of claim 1 wherein the defining a window comprises identifying a Q-wave in the electrocardiogram.

6. The method of claim 1 wherein the defining a window comprises identifying a T-wave in the electrocardiogram.

7. The method of claim 1 wherein the defining a window comprises defining a window based on a Q-wave and a T-wave.

8. The method of claim 1 wherein the window enhances accuracy in determination of a time of peak motion of the electrode as being related to an intrinsic or paced activation of the heart.

9. The method of claim 1 further comprising adjusting a cardiac therapy based at least in part on the time of peak motion.

10. The method of claim 1 further comprising identifying motion due to respiration based on a predefined respiratory motion direction in the cardiac coordinate system.

11. The method of claim 10 wherein defining the respiratory motion direction comprises performing a principal component analysis.

12. The method of claim 10 wherein the analyzing the position information comprises accounting for respiratory motion.

13. The method of claim 10 wherein the defining a window comprises defining a window based on the electrocardiogram and respiratory motion.

14. One or more non-transitory computer-readable media comprising processor executable instructions to instruct a computing device to: access an electrocardiogram of a patient; access position information with respect to time, the position information acquired via an electrode located in a venous network of the patient; define a window based on the electrocardiogram; and analyze the position information, with respect to a cardiac coordinate system, within the defined window to determine a time of peak motion of the electrode.

* * * * *